(12) United States Patent
Zheng et al.

(10) Patent No.: US 10,251,831 B2
(45) Date of Patent: *Apr. 9, 2019

(54) EXTRACT FOR TREATING WRINKLES AND/OR FINE LINES

(71) Applicant: Avon Products, Inc., Suffern, NY (US)

(72) Inventors: Qian Zheng, Morris Plains, NJ (US); Russell J. Wyborski, Pine Island, NY (US); Uma Santhanam, Tenafly, NJ (US); John W. Lyga, Basking Ridge, NJ (US); Dmitri S. Ptchelintsev, Jersey City, NJ (US); Siming W. Chen, Basking Ridge, NJ (US)

(73) Assignee: Avon Products, Inc., Suffern, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/675,891

(22) Filed: Apr. 1, 2015

(65) Prior Publication Data

US 2015/0202146 A1 Jul. 23, 2015

Related U.S. Application Data

(62) Division of application No. 13/602,557, filed on Sep. 4, 2012, now Pat. No. 9,066,896, which is a division of application No. 12/966,098, filed on Dec. 13, 2010, now Pat. No. 8,394,427.

(60) Provisional application No. 61/290,720, filed on Dec. 29, 2009, provisional application No. 61/289,038, filed on Dec. 22, 2009.

(51) Int. Cl.
| | |
|---|---|
| *A61K 36/28* | (2006.01) |
| *A61K 8/97* | (2017.01) |
| *A61K 8/49* | (2006.01) |
| *A61K 36/00* | (2006.01) |
| *A61Q 19/08* | (2006.01) |
| *A61K 8/34* | (2006.01) |
| *C12Q 1/6881* | (2018.01) |

(52) U.S. Cl.
CPC .......... *A61K 8/97* (2013.01); *A61K 8/342* (2013.01); *A61K 8/4906* (2013.01); *A61K 8/4926* (2013.01); *A61K 36/00* (2013.01); *A61Q 19/08* (2013.01); *C12Q 1/6881* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,146,640 A | 11/2000 | Dyke | |
| 7,618,662 B2 | 11/2009 | Hines et al. | |
| 8,128,914 B2 * | 3/2012 | Ptchelintsev | A61Q 19/08 424/59 |
| 8,394,427 B2 * | 3/2013 | Zheng | A61K 8/4906 424/725 |
| 8,512,764 B2 | 8/2013 | Paufique | |
| 8,802,167 B2 * | 8/2014 | Hwang | A61K 8/97 424/725 |
| 9,034,396 B2 | 5/2015 | Zheng et al. | |
| 9,066,896 B2 * | 6/2015 | Zheng | A61K 8/4906 |
| 9,186,316 B2 | 11/2015 | Khusial et al. | |
| 9,238,000 B2 | 1/2016 | Khusial et al. | |
| 2003/0207818 A1 | 11/2003 | Jia et al. | |
| 2004/0156886 A1 * | 8/2004 | Kose | A61K 9/7061 424/449 |
| 2005/0191267 A1 | 9/2005 | Luanratana | |
| 2006/0134231 A1 | 6/2006 | Hines et al. | |
| 2006/0193819 A1 * | 8/2006 | Lu | A61K 8/97 424/74 |
| 2006/0257351 A1 | 11/2006 | Chiba | |
| 2007/0224272 A1 | 9/2007 | Touitou | |
| 2008/0274453 A1 | 11/2008 | Hageman | |
| 2010/0158828 A1 * | 6/2010 | Ptchelintsev | A61Q 19/08 424/59 |
| 2012/0003332 A1 | 1/2012 | Zheng et al. | |
| 2013/0053423 A1 | 2/2013 | Lyga | |
| 2013/0102606 A1 | 4/2013 | Hwang et al. | |
| 2013/0149268 A1 | 6/2013 | Chen et al. | |
| 2013/0149397 A1 | 6/2013 | Chen et al. | |
| 2014/0161910 A1 | 6/2014 | Zheng et al. | |
| 2014/0255523 A1 * | 9/2014 | Ptchelintsev | A61K 8/97 424/725 |

FOREIGN PATENT DOCUMENTS

| | | |
|---|---|---|
| CN | 1895213 A | 1/2007 |
| CN | 101039579 A | 9/2007 |
| CN | 101143166 A | 3/2008 |
| CN | 101559033 A | 10/2009 |
| EP | 2067467 A2 | 6/2009 |

(Continued)

OTHER PUBLICATIONS

Wang, Bing Hui et al., "Specific Inhibition of Cyclic Amp-Dependent Protein Kinase by Warangalone and Robustic Acid," Phytochemistry, vol. 44, No. 5, pp. 787-796 (1997).
Weinbaum et al., "Deficiency in Microfibril-associated Glycoprotein-1 Leads to Complex Phenotypes in Multiple Organ Systems," Journal of Biological Chemistry, vol. 283, No. 37, pp. 25533-25543 (2008).
Liu Changsuo et al., "Structure and function of paxillin", Chemistry of Life, vol. 25, No. 3, Jun. 15, 2005, pp. 208-210.
Tang Yanhong, et al., "Protection effect of human epidermal growth factor on skin", Chinese Journal of Medical Aesthetics and Cosmetology, vol. 10, No. 1, Feb. 15, 2004, pp. 53-55.

(Continued)

*Primary Examiner* — Ralph J Gitomer
(74) *Attorney, Agent, or Firm* — Brian P. McCloskey

(57) ABSTRACT

Cosmetic compositions comprising one or more paxillin stimulators and methods of using such compositions to impart anti-aging benefits to the skin are disclosed. The paxillin stimulators and combinations thereof are believed to have modulatory activity against at least one biochemical pathway implicated in skin aging.

8 Claims, 1 Drawing Sheet

Specification includes a Sequence Listing.

(56) References Cited

FOREIGN PATENT DOCUMENTS

| | | | |
|---|---|---|---|
| JP | 48022638 B1 | | 7/1973 |
| JP | H0558874 A | | 3/1993 |
| JP | H1192331 A | | 4/1999 |
| JP | 2002087973 A | | 3/2002 |
| JP | 2003113027 A | | 4/2003 |
| JP | 2003113064 A | | 4/2003 |
| JP | 2006069954 A | | 3/2006 |
| JP | 2007016003 A | | 1/2007 |
| JP | 2009/13128 A | * | 1/2009 |
| JP | 2012 246324 | * | 1/2009 |
| JP | 2010090069 A | | 4/2010 |
| KR | 20050068068 A | | 7/2005 |
| KR | 20050068588 A | | 7/2005 |
| WO | 2000053156 A1 | | 9/2000 |
| WO | 2006068778 A2 | | 6/2006 |
| WO | 2007/045060 A1 | | 4/2007 |
| WO | 2007093839 A1 | | 8/2007 |
| WO | 2008102998 A1 | | 8/2008 |
| WO | 2009048282 A2 | | 4/2009 |
| WO | 2010075004 A1 | | 7/2010 |
| WO | 2011081698 A1 | | 7/2011 |
| WO | 2012005872 A1 | | 1/2012 |

OTHER PUBLICATIONS

"Effect of Simvastatin on Reorganization of Facial Adhesion and Actin Cytoskeleton in Vascular Smooth Muscleel Cells Induced by . . . ", Chinese Journal of Obstetrics & Gynecology and Pediatrics, vol. 4, No. 5, Oct. 1, 2008, pp. 12-15.

Kang et al., "Topical N-Acetyl Cysteine and Genistein Prevent Ultraviolet-Light-Induced Signaling That Leads to Photoaginig in Human Skin in vivo," The Society for Investigative Dermatology, Inc., vol. 120, No. 5, pp. 835-841 (2003).

Nanasombat et al., "Antimicrobial, antioxidant and anticancer activities of Thai local vegetables," Journal of Medicinal Plants Research, vol. 3, No. 5, pp. 443-449 (2009).

Singthong et al., "Extraction and physicochemical characterisation of polysaccharide gum from Yanang (*Tiliacora triandra*) leaves," Food Chemistry, vol. 114, pp. 1301-1307 (2009).

Choi, Eun-Mi et al., "Screening of Indonesian medicinal plants for inhibitor activity on nitric oxide production of RAW264.7 cells and antioxidant activity," Fitoterapia, vol. 76, pp. 194-203 (2005).

Fujimoto, Norihiro et al., "Expression of microfibril-associated glycoprotein-1 (MAGP-1) in human epidermal keratinocytes," Arch. Dermatol. Res. vol. 292, pp. 21-26 (2000).

Jothi, G. J. et al., "Glimpses of Tribal Botanical Knowledge of Tirunelveli Hills, Western Ghats, India," Ethnobotanical Leaflets, vol. 12, pp. 118-126 (2008).

Micor, Jose Rene L. et al., "Biological Activity of Bignay [*Antidesma bunius* (L.) Spreng] Crude Extract in Artemia salina," J. Med. Sci., vol. 5, No. 3, pp. 195-198 (2005).

Mintel, "Treatment Cream," Database GNPD [online], database accession No. 1646948 (2011).

Tatano, Yutaka et al., "Significant Decrease in Tropoelastin Gene Expression in fibroblasts from a Japanese Costello Syndrome Patient with Impaired Elastogenesis and Enhanced Proliferation," J. Biochem., vol. 140, pp. 193-200 (2000).

U.S. Appl. No. 12/342,197, filed Dec. 23, 2008, Ptchelintsev, Dmitri S, U.S. Pat. No. 7,993,629, Aug. 9, 2011.

U.S. Appl. No. 12/966,098, filed Dec. 13, 2010, Zheng, Quian, U.S. Pat. No. 8,394,427, Mar. 12, 2013.

U.S. Appl. No. 13/165,876, filed Jun. 22, 2011, Ptchelintsev, Dmitri S, U.S. Pat. No. 8,128,914, Mar. 6, 2012.

U.S. Appl. No. 13/305,779, filed Nov. 29, 2011, Zheng, Qian.

U.S. Appl. No. 13/710,536, filed Dec. 11, 2012, Hwang, Cheng et al.

U.S. Appl. No. 13/710,617, filed Dec. 11, 2012, Zheng, Qian et al.

U.S. Appl. No. 13/158,947, filed Jun. 13, 2011, Zheng, Qian et al.

U.S. Appl. No. 13/216,626, filed Aug. 24, 2011, Thorn Leeson, Daniel.

U.S. Appl. No. 14/055,037, filed Oct. 16, 2013, Khusial, Permanan Raaj.

U.S. Appl. No. 14/066,862, filed Oct. 30, 2013, Lyga, John W. et al.

U.S. Appl. No. 09/722,782, filed Nov. 27, 2000, Duggan, Michele, U.S. Pat. No. 6,583,184, Jun. 24, 2003.

U.S. Appl. No. 07/079,060, filed Jul. 29, 2987, Dulak, Michael et al., U.S. Pat. No. 4,888,363, Dec. 19, 1989.

U.S. Appl. No. 12/648,581, filed Dec. 29, 2009, Lyga, John et al.

U.S. Appl. No. 13/602,557, filed Sep. 4, 2012, Zheng, Qian.

U.S. Appl. No. 12/827,001, filed Jun. 30, 2010, Ptchelintsev, Dmitri, U.S. Pat. No. 8,771,758, Jul. 8, 2014.

U.S. Appl. No. 14/284,869, filed May 22, 2014, Ptchelintsev, Dmitri.

U.S. Appl. No. 14/661,061, filed Mar. 18, 2015, Khusial, Permanan Raaj.

U.S. Appl. No. 14/669,545, filed Mar. 25, 2015, Lyga, John.

\* cited by examiner

(A)
(B)

```
                        SEQUENCE LISTING

<160> NUMBER OF SEQ ID NOS: 3

<210> SEQ ID NO 1
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gggaagacgt ggcacccctc ccggaacttc ttcgagcccc gcgctgctac tactgcaacg      60
gccccatcct ggaagccttc tttggtcccg aaaacggcag cttcttcgag c              111

<210> SEQ ID NO 2
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gagcacttcg tctgcaccca ctgccaggag gagatcggat aaagtggtga cagcccttga      60
ccggacgtgg caccctgagg gttccacgag aaggacggca aggcctactg tcgcaagtgc     120
tttgtgtgcc gggaatgctt cacgccattc gtgacgacgg gcagccctac tgtgaggtgc     180
actaccacga gc                                                         192

<210> SEQ ID NO 3
<211> LENGTH: 120
<212> TYPE: DNA
<213> ORGANISM: Artificial Sequence
<220> FEATURE:
```

-continued

```
<223> OTHER INFORMATION: Description of Artificial Sequence: Synthetic
      polynucleotide

<400> SEQUENCE: 3
acacttcttc tgtgcacagt gtggggacta cttcgacatg ttcgcaccca agtgtggcgg      60
ctgcgcccgg gccatcctgg agaactatat ctcagccctc aacacgctgt ggcatcctga     120
```

EXTRACT FOR TREATING WRINKLES AND/OR FINE LINES

This application is a divisional of, and claims priority to, U.S. patent application Ser. No. 13/602,557, filed Sep. 4, 2012, which is a divisional of U.S. patent application Ser. No. 12/966,098, now U.S. Pat. No. 8,394,427, filed Dec. 13, 2010, which claims priority to U.S. Provisional Patent Applications Ser. No. 61/290,720, filed Dec. 29, 2009; and 61/289,038, filed Dec. 22, 2009. Each of the aforementioned applications is hereby incorporated by reference in its entirety.

FIELD OF THE INVENTION

The present invention relates generally to compositions for topical application to the skin which comprise at least one paxillin stimulator and the use of such compositions to provide benefits to the skin, in particular, to provide anti-aging benefits to human skin.

BACKGROUND OF THE INVENTION

Consumers continually seek to improve the appearance of their skin and in particular to reduce visible signs of skin aging. Unwanted signs include lines and wrinkles, skin sagging or atrophy, and loss of suppleness, and there remains a need for products that combat such signs of aging and, more generally, that provide anti-aging and/or anti-wrinkle effects.

Recent studies have revealed that dermal fibroblasts undergo morphology changes and cell body collapse in both chronically and photo-aged skin. See, e.g., Varani et al., 2004. J. Invest. Dermatol. 122:1471-9; and Varani et al., 2006. Am. J. Pathol. 168: 1861-8. Such alterations can lead to coarse, rough, and wrinkled appearance, which are characteristics of aged skin. Further studies suggest that collagen degradation along with altered integrin and focal adhesion molecules are factors contributing to the loss of a functional dermal collagen matrix, with the consequence of cell body collapse due to a loss of mechanical tension between fibroblasts and the matrix. See, e.g., Fisher et al., 2008. Arch Dermatol. 144:666-72.

Paxillin is an important adaptor protein that mediates transmembrane integrins and growth factor signaling. It transduces messages from the extracellular matrix, recruits other focal adhesion molecules to form complexes, and activates intracellular cytoskeleton assembly. Brown et al., 2004. Physiol Rev. 84:1315-39. This process is important for cell adhesion and migration, as well as muscle contraction. Paxillin-mediated signaling also affects long-term changes in gene expression, cell proliferation, and extracellular matrix organization, which is important to wound repair and tissue regeneration.

Paxillin exists in higher eukaryotes as three isoforms. Paxillin α is the principle, ubiquitously expressed isoform, expressed in most adult human tissues other than brain; paxillin β- and γ-isoforms are restrictively expressed. A fourth isoform, paxillin δ, is found mainly in epithelial cells. The paxillin proteins are comprised of multiple protein-binding motifs, corresponding to multiple protein-protein interaction and protein recognition sites, with many phosphorylation sites dispersed throughout the molecule. Paxillin binding partners range from structural actin-binding proteins, such as vinculin, to signaling molecules such as focal adhesion kinase (FAK) and integrin-linked kinase (ILK). Paxillin is phosphorylated at the multiple tyrosine, serine, and threonine sites in response, e.g., to cell adhesion and/or various soluble growth factors and cytokines and is thought to be at the signaling crossroads of cell adhesion and growth factor modulation under normal conditions.

Following exposure to oxidative stress, abnormalities have been observed in paxillin phosphorylation and cytoskeletal organization in cultured cells. Hao et al., 2006. Free radical Biol Med. 41:302-10; and Zhou et al., 1999. J Cell Physiol. 180:182-9. Also, altered levels and altered localization of various focal adhesion proteins have been observed in senescent cells in vitro. Nishio et al., 2005. Histochem cell biol. 123:263-73. Nonetheless, no direct relation has been implicated between paxillin expression and visible signs of aging in human skin.

It is therefore an object of the invention to provide new approaches for combating signs of skin aging through paxillin-mediated pathways. It is a further object of the invention to provide new compositions and methods directed thereto. It is a still further object of the invention to improve the overall appearance of skin, including treating, reversing, and/or preventing signs of aging, using cosmetic compositions comprising effective amounts of one or more compounds that affect paxillin production.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that disruption of normal paxillin production in human skin fibroblasts directly leads to changes in cell shape, indicating an essential role of paxillin in maintaining optimum cell morphology and optimum cell health. It further has surprisingly been found that paxillin levels in human skin cells can be stimulated by topical application of compositions comprising one or more paxillin stimulators, indicating a new approach to combat signs of skin aging.

In one aspect of the invention, cosmetic compositions are provided for improving the aesthetic appearance of skin comprising, in a cosmetically acceptable vehicle, an effective amount of at least one paxillin stimulator. The paxillin stimulator may be selected from the group consisting of pyridone-fused azabicyclic compounds having the structure of formulae IV or V; *Jasminum sambac* extract; *Coccinia grandis* extract; *Eliptica prostrata* Linn. extract; *Clitoria ternatea* Linn. extract; *Ozothamnus obcordatus* extract; *Erythrina flabelliformis* extract; *Lonchocarpus capassa* extract; *Sophora tomentosa* extract; *Trifolium hybridum* extract; *Eremophila mitchellii* extract; *Kunzea ambigua* extract; Tanshinone IIA; Tetrandrine; Carvacrol; cis-6-Nonenol; Retinyl punicate; Retinyl oleate; Equol; MycoFusions Coriolus Black Corn Biomass; MycoFusions Maitake Waxy Hulless Barley Biomass; *Zanthoxylum nitidium* extract; *Ophiopogon Thunb.* P.E. extract; *Radix platycodonis* extract; *Terminalia belerica* extract; *Cocculus glaucescens* extract; *Stephania* solid extract; and Rosemary extract. In some embodiments, the cosmetic composition comprises one or more paxillin stimulators, and in other embodiments, the cosmetic composition comprises two or more paxillin stimulators.

In some embodiments, the cosmetic composition comprises cis-6-nonenol as the paxillin stimulator in an amount effective to improve the aesthetic appearance of skin, such as to impart an anti-aging benefit to the skin. In another embodiment, the cosmetic comoposition comprises cis-6-nonenol as a first paxillin stimulator and at least one other paxillin stimulator, the cis-6-nonenol and the other paxillin stimulator being present in the composition in an aggregate amount effective to impart an anti-aging benefit to the skin In some embodiments, one of more of the substances of the group are excluded from the cosmetic composition. For example, in some embodiments, the composition does not include *Trifolium hybridum* extract and/or does not include retinyl oleate and/or does not include Equol.

In some embodiments, the cosmetic composition further comprises at least one other skin active, said skin active being selected from the group consisting of botanicals, keratolytic agents, desquamating agents, keratinocyte proliferation enhancers, elastase inhibitors, depigmenting agents, anti-inflammatory agents, steroids, anti-acne agents, antioxidants, salicylic acid or salicylates, thiodipropionic acid or esters thereof, advanced glycation end-product (AGE) inhibitors, and alpha-hydroxyacids. In some embodiments, the cosmetic composition further comprises a collagen stimulator, such as TDPA.

In another aspect, the invention relates to methods comprising topically applying to the skin a cosmetic composition comprising one or more paxillin stimulators. The cosmetic composition will comprise an effective amount of at least one paxillin stimulator to provide an anti-aging benefit to human skin, such as, to treat, reverse, ameliorate and/or prevent signs of skin aging. Anti-aging benefits include without limitation, the following:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in skin texture and/or promotion of re-texturization;
(h) improvement in skin barrier repair and/or function;
(i) treatment and/or prevention of skin sagging or atrophy; and/or
(j) improvement in appearance of skin contours;
(k) restoration of skin luster and/or brightness;
(l) replenishment of essential nutrients and/or constituents in the skin;
(m) improvement of skin appearance decreased by menopause;
(n) improvement in skin moisturization and/or hydration; and
(o) improvement of skin elasticity and/or resiliency.

Also provided is a method for imparting an anti-aging benefit to human skin comprising topically applying to skin in need thereof a composition comprising at least one paxillin stimulator in an amount effective to increase paxillin level in dermal fibroblasts, e.g., by up-regulating paxillin expression. Skin in need thereof can photo-aged and/or skin damaged by UV radiation.

In another aspect of the invention, a method of treating, reversing, ameliorating and/or preventing fine lines or wrinkles or sagging in human skin is provided, comprising topically applying to skin in need thereof, including applying directly to a wrinkle or fine line, a composition comprising at least one paxillin stimulator in an amount effective to increase the level of paxillin in dermal fibroblasts.

In still another aspect, the invention relates to methods and compositions for assaying whether a candidate material is a paxillin stimulator. Screening methods can comprise contacting a human skin cell with a candidate material and assaying for up-regulation of paxillin mRNA. Assaying for up-regulation of paxillin mRNA may comprise a branched DNA technology using labeled probes specifically designed to identify paxillin mRNA. In some embodiments, the probes comprise nucleotide sequences that together cover the paxillin mRNA sequence. In some embodiments, for example, the probes comprise nucleotide sequences according to SEQ ID NOS: 1, 2, and/or 3, disclosed herein, and/or variations thereof. Still other aspects of the invention relate to candidate materials identified as paxillin stimulators, e.g., candidate materials identified as up-regulating paxillin mRNA using one or more probes, compositions, and/or methods described herein.

In still another aspect, the invention relates to methods for formulating a cosmetic composition for imparting an anti-aging benefit to human skin comprising assaying to determine if a candidate material is a paxillin stimulator; and, if so, incorporating the material into a cosmetically acceptable vehicle. In some embodiments, the candidate material is a plant extract.

These and other aspects of the present invention will be better understood by reference to the following detailed description.

BRIEF DESCRIPTION OF THE DRAWINGS

FIG. 1 illustrates human skin biopsies showing paxillin protein levels after topical treatment with (A) a control vehicle; and (B) a candidate paxillin stimulator.

DETAILED DESCRIPTION

It has surprisingly been found that compositions comprising one or more substances that stimulate paxillin can be topically applied to human skin to improve the aesthetic appearance of the skin, in particular, to treat, reverse, and/or prevent visible signs of aging. Novel substances as well as a number of substances previously known in the cosmetic arts have surprisingly been found to stimulate paxillin and hence will find use in topical cosmetic compositions with anti-aging benefits.

In view of these findings and others, a topical composition comprising one or more paxillin stimulators is contemplated to be useful in combating signs of skin aging, including reducing fine lines and wrinkles, preserving skin suppleness and softness, preventing skin sagging or atrophy, improving skin plumpness and/or tautness and counteracting other signs of skin aging and/or skin damage. It is further contemplated that other substances that stimulate paxillin production or otherwise promote increased intracellular paxillin levels in dermal fibroblasts can find use in anti-aging topical compositions, according to the instant disclosure. As used herein, "consisting essentially of" means that the composition or component may include additional ingredients, but only if the additional ingredients do not materially alter the basic and novel characteristics of the claimed compositions or methods.

Paxillin Stimulating Compounds and Compositions

One aspect of the present invention relates to compositions for topical application which comprise one or more paxillin stimulators to impart an anti-aging benefit to the skin, such as treating, reversing, ameliorating, delaying and/or preventing signs of skin aging. Combating signs of skin aging may include without limitation, the following:

(a) treatment, reduction, and/or prevention of fine lines or wrinkles;

(b) reduction of skin pore size;

(c) improvement in skin thickness, plumpness, and/or tautness;

(d) improvement in skin suppleness and/or softness;

(e) improvement in skin tone, radiance, and/or clarity;

(f) improvement in procollagen and/or collagen production;

(g) improvement in skin texture and/or promotion of retexturization;

(h) improvement in skin barrier repair and/or function;

(i) treatment and/or prevention of skin sagging or atrophy; and/or (j) improvement in appearance of skin contours;

(k) restoration of skin luster and/or brightness;

(l) replenishment of essential nutrients and/or constituents in the skin;

(m) improvement of skin appearance decreased by menopause;

(n) improvement in skin moisturization and/or hydration; and (o) improvement of skin elasticity and/or resiliency.

In practice, the compositions of the invention are applied to skin in need of treatment, that is, skin which suffers from a deficiency or loss in any of the foregoing skin attributes or which would otherwise benefit from improvement in any of the foregoing skin attributes.

A "paxillin stimulator" refers to any agent that can increase the level of paxillin in human dermal fibroblasts. Increase in paxillin levels can refer to an increase in paxillin mRNA transcribed and/or an increase in paxillin protein expressed in the fibroblast, in vitro or in vivo, and can be measured by any means known in the art, or as described herein. For example, the paxillin stimulator can act as an up-regulator of paxillin expression within dermal fibroblasts. See, e.g., Example 1 below. In some embodiments, paxillin level is increased by at least about 10%, at least about 20%, at least about 60%, at least about 80%, at least about 100%, at least about 150%, at least about 200%, at least about 250%, or at least about 300%, compared to the level of paxillin in the absence of the paxillin stimulator. A "paxillin stimulator" may also include agents that bring about an effective increase in paxillin levels by, e.g., increasing the stability of paxillin RNA and/or protein, and/or increasing localization of paxillin to sites of action.

The paxillin stimulator may be any organic or inorganic compound, small molecule, macromolecule, macromolecular complex, cellular lysate, sub-cellular compartment, extract of biological origin, or combination thereof.

In some embodiments, the paxillin stimulator comprises an organic molecule. In some embodiments, the paxillin stimulator comprises a pyridone-fused azabicyclic compound, or a pharmaceutically or cosmetically acceptable salts and/or prodrug thereof. The pyridone-fused azabicyclic compounds include, without limitation, the paxillin-stimulating compounds according to formula (I):

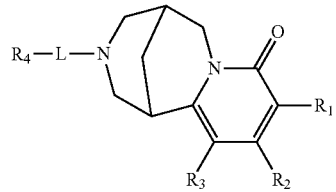

wherein, $R_1$, $R_2$, $R_3$, and $R_4$ are independently selected from hydrogen; —R; halogen (—F, —Cl, —Br, —I); —OH; —C≡C—R; —C≡N; —C(R)=N—$R^N$; —C=N—N($R^N$)$_2$; —C(=N$R_N$)—N($R^N$)$_2$; —CH$_2$OH; —CHO; —(C=O)—R; —CO$_2$H; —CO$_2$—; —CO$_2$R; —CS$_2$R; —(C=O)—S—R; —S—(C=O)—R; —(C=O)—NH$_2$; —(C=O)—N$R^N R^N$; —(C=O)—NHNH$_2$; —O—(C=O)—NHNH$_2$; —(C=S)—NH$_2$; —(C=S)—N($R^N$)$_2$; —O—(C=O)—H; —O—(C=O)—R; —O—(C=O)—NH$_2$; —O—(C=O)—N$R^N R^N$; —OR; —SR; —NH$_2$; —NH$R^N$; —N($R^N$)$_2$; —N($R^N$)$_3^+$; —N($R^N$)—OH; —N(→O)(R)$_2$; —O—N($R^N$)$_2$; —N($R^N$)—O—R; —N($R^N$)—N($R^N$)$_2$; —$NR^N$—(C=O)—R; —$NR^N$C(=O)O—R; —$NR^N$—CHO; —$NR^N$—(C=O)—R; —$NR^N$C(=O)O—R; —$NR^N$C(=O)N$R^N$; —N($R^N$)—C(=O)—N($R^N$)$_2$; —N($R^N$)—C(=S)—N($R^N$)$_2$; —N=CR$_2$; -N=N—$R^N$; —SCN; —NCS; —NSO; —SS—R; —SO—R; —SO$_2$—R; —O—S(=O)$_2$—R; —S(=O)$_2$—OR; —N($R^N$)—SO$_2$—R; —SO$_2$—N(R)$_2$; —O—SO$_3^-$; —O—S(=O)$_2$—OR; —O—S(=O)—OR; —O—S(=O)—R; —S(=O)—OR; —S(=O)—R; —NO; —NO$_2$; —NO$_3$; —O—NO; —O—NO$_2$; —N$_3$; —N$_2$; —N(C$_2$H$_4$); —Si(R)$_3$; —CF$_3$; —O—CF$_3$; —(C=O)—R; —PR$_2$; —O—P(=O)(OR)$_2$; and —P(=O)(OR)$_2$; and where any two adjacent groups $R_1$, $R_2$ and $R_3$ may together form a five- or six-membered ring fused to the pyridone ring;

L is either a bond (i.e., L is omitted), or is a moiety selected from the group consisting of —(C=O)—, —C(O)—O—, —(C=O)—$NR^N$—, —(CH$_2$)$_a$—, —(C=O)—(CH$_2$)$_a$—C(O)—, —(C=O)—(CH$_2$)$_a$—, —(CH$_2$)$_a$—C(O)—, where "a" is an integer from 1 to 6; and where L is preferably —(C=O)—;

and R and $R^N$ are selected independently at each occurrence from hydrogen or a $C_1$-$C_{30}$ hydrocarbon radical, optionally including from 1-20 heteroatoms, such as oxygen, sulfur, and nitrogen atoms; where R and $R^N$ are preferably selected from substituted or unsubstituted, branched, straight chain or cyclic, $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, aryl-heteroaryl, bicyclic alkyl, aryl, or heteroaryl radicals, and combinations thereof; and wherein each of the foregoing radicals may be substituted with 1-6 heteroatoms and/or with any heteroatom-containing moiety, including, for example, acyl, acyloxy, amino, alkoxyl, alkylamino, alkylthiol, alkylimino, alkylsulfonate, amide, azo, carboxyl, carboxamide, carbamide, cyano, dialkylamino, ester, halogen, hydroxyl, nitro, oxo, oxa, oxime, perfluoro, phosphate, phosphonyl, phosphinyl, sulfate, sulfate, sulfo-alkyl, thiol, thioether, thioester, thioalkoxy, thiocyanate, and combinations thereof.

In some embodiments according to formula (I), $R_1$ is a group —R, where R is preferably selected from substituted or unsubstituted, branched, straight chain or cyclic, $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, aryl-heteroaryl, bicyclic alkyl, aryl, or heteroaryl radicals, and combinations thereof; and wherein each of the foregoing radicals may be substituted with 1-6 heteroatoms and/or with any heteroatom-containing moiety, including, for example, acyl, acyloxy, amino, alkoxyl, alkylamino, alkylthiol, alkylimino, alkylsulfonate, amide, azo, carboxyl, carboxamide, carbamide, cyano, dialkylamino, ester, halogen, hydroxyl, nitro, oxo, oxa, oxime, perfluoro, phosphate, phosphonyl, phosphinyl, sulfate, sulfo-alkyl, thiol, thioether, thia, thioalkoxy, thiocyanate, and combinations thereof.

R may comprise, for example, aliphatic $C_1$-$C_{20}$ hydrocarbon radicals; including aliphatic $C_1$-$C_{12}$ hydrocarbon radicals, aliphatic $C_1$-$C_8$ hydrocarbon radicals, or aliphatic $C_1$-$C_6$ hydrocarbon radicals, as exemplified by substituted or unsubstituted branched, straight chain or cyclic, alkyl, alkenyl (e.g., vinyl, allyl, etc.), and alkynyl moieties; $C_6$-$C_{20}$ aromatic hydrocarbon radicals, including $C_6$-$C_{12}$ aromatic hydrocarbon radicals, $C_6$-$C_{10}$ aromatic hydrocarbon radicals, or $C_6$ aromatic hydrocarbon radicals, as exemplified by substituted or unsubstituted aryl (e.g., phenyl), alkyl-aryl (e.g., benzyl), aryl-alkyl (e.g., toluyl), and the like; or $C_1$-$C_{20}$ heteroaryl radicals including one or more heteroatoms selected from O, N, and S in the ring; including $C_1$-$C_{12}$ heteroaromatic radicals, $C_1$-$C_8$ heteroaromatic radicals, and $C_1$-$C_6$ heteroaromatic radicals, as exemplified by heteroaryl, alkyl-heteroaryl, heteroaryl-alkyl and the like. In some embodiments, R may be, for example, independently at each occurrence, hydrogen, methyl, ethyl, propyl, butyl, pentyl, hexyl, phenyl, benzyl, or the like, including halo and perhalo derivatives thereof.

In some embodiments, $R_2$ and/or $R_3$ will be hydrogen. In some embodiments, L is a group —(C=O)—. In other embodiments according to formula (I), $R_1$ is a group —R, where R is an aryl or heteroaryl group, either of which may be optionally substituted with a group —R and/or with 1-6 heteroatoms and/or with any of the heteroatom-containing moieties described above. Typically, where R is an aryl or heteroaryl group, the ring will comprise five or six atoms in the ring system. In particular, paxillin-stimulating compounds according to formula (II) are contemplated to be useful:

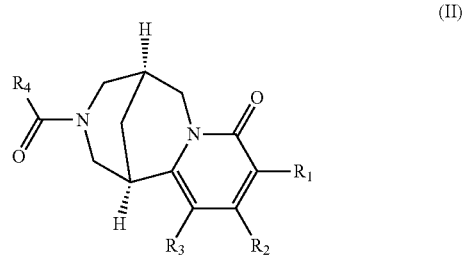

(II)

where $R_1$ is as defined above, or is a group -Q(-R*)$_n$, where Q is ring having three, four, five or six atoms in the ring, including aromatic or heteroaromatic rings, and R* represents substitution on the ring and is as defined above for R and is independently selected at each occurrence. The substituents on ring Q, represented by R*, may be attached to any available ring atom, except for the point of attachment to the pyridone in the case of aromatic and heteroaromatic rings Q. The number of substituents is determined by "n" which is an integer from 0 (i.e., R* is absent) to 5, depending on the number of positions available for substitution on the ring; and where $R_2$, $R_3$ and $R_4$ are as defined above. In some embodiments according to formula (II), $R_2$ and/or $R_3$ are hydrogen.

Non-limiting examples of three-membered heterocyclic rings, include but are not limited to, aziridine, oxirane, thiirane, diaziridine, and oxaziridine. Non-limiting examples of four-membered heterocyclic rings, include but are not limited to, azetidine, oxetane, thietane, diazetidine, oxazetidine, and 1,2-oxathietane.

Five membered heterocycles represent a currently preferred embodiment of the invention for the substituent Q. Non-limiting examples of five-membered heterocyclic rings include, without limitation, pyrrolidine, tetrahydrofuran, tetrahydrothiophene, oxazolidine, thiazolidine, 1,3-dioiane, 1,3-oxzthiolane, 1,3-dithiolane, imidazolidine, pyrazolidine, pyrrole, furan, thiophene, oxazole, isoxazole, thiazole, isothiazole, imidazole, pyrazole, 1,3,4-oxadiazole, 1,2,4-oxadiazole, 1,3,4-thiadiazole, 1,2,4-thiadiazole, 1,3,4-triazole, 1,2,3-triazole, and the like. Q may be selected from, for example, the following five membered heterocylic rings which are aromatic, fully saturated, or comprises one, or two double bonds:

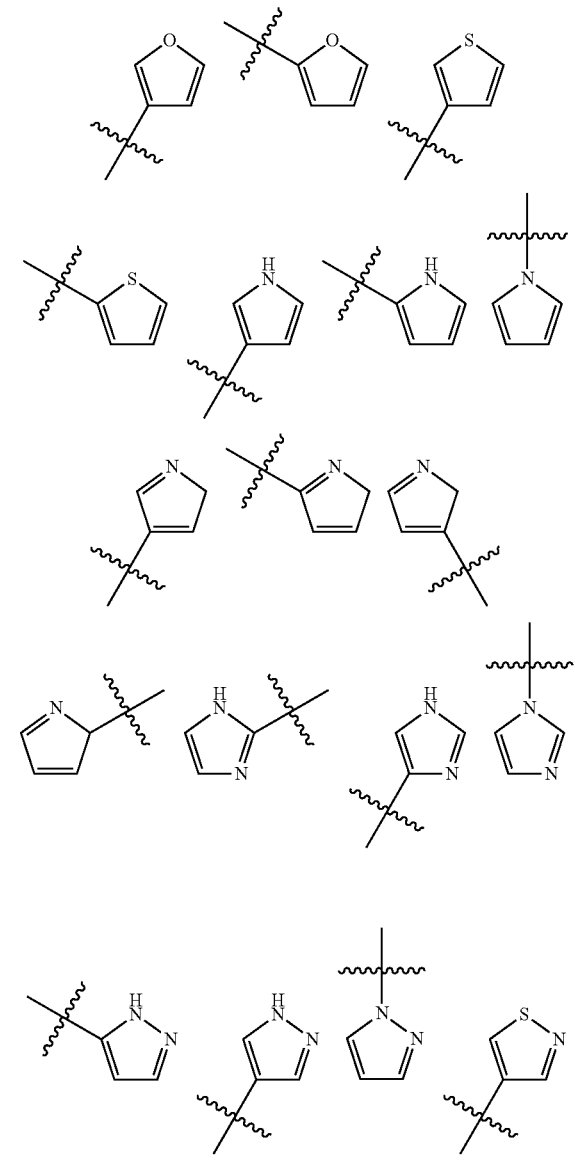

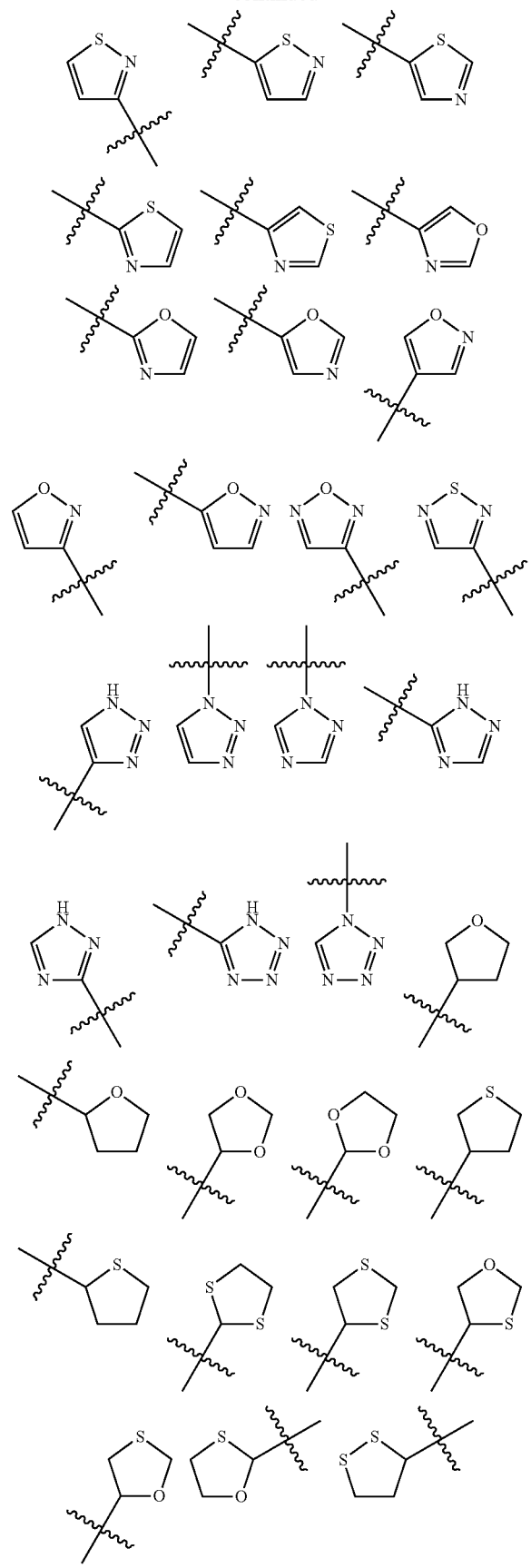
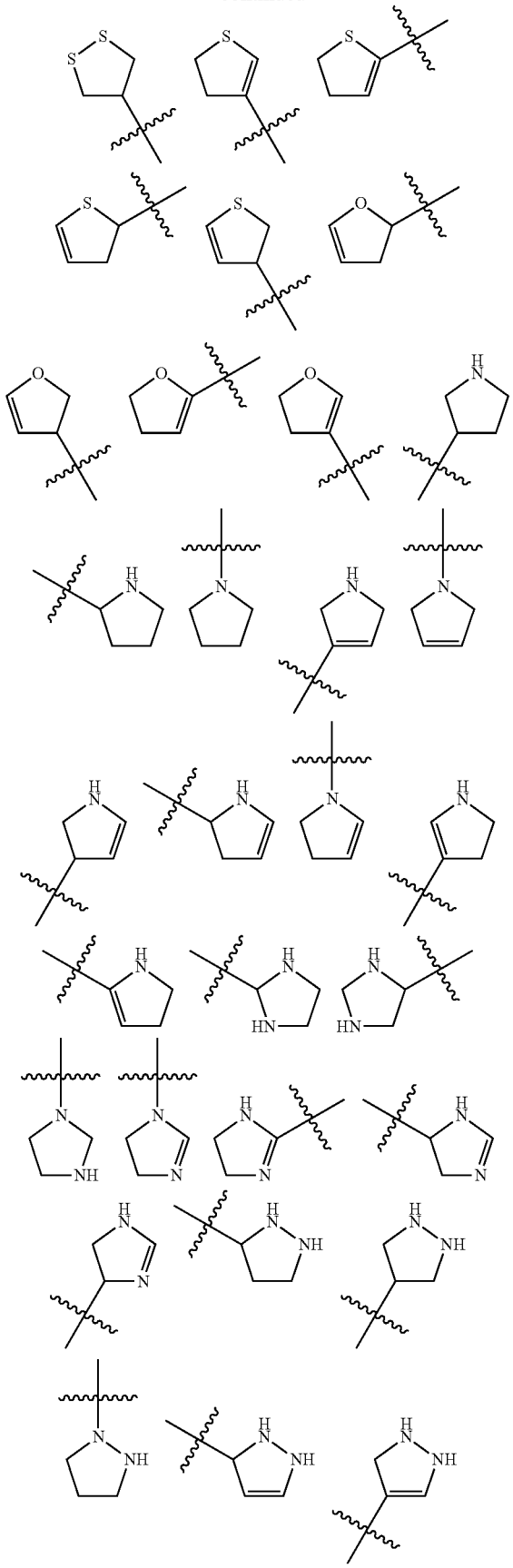

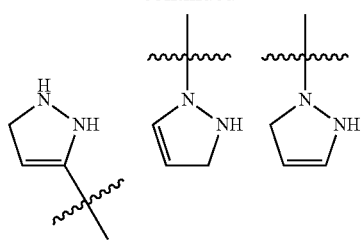

These five membered rings may be optionally functionalized with one or more groups R*, as defined above, with particular mention being made of $C_{1-4}$ alkyl (e.g., methyl, ethyl, isopropyl, etc.), $C_{1-4}$ alkoxyl, halo, hydroxyl, oxo, thiol, amino, alkylamino, dialkylamino, —$CH_2$—$N(CH_3)_2$, —$(CH_2)_{1-6}$—$N(R^N)_2$, —(C=O)—H, —(C=O)—R, —(C=O)—$CH_3$, —(C=O)—$CH_2CH_3$, —O—(C=O)—R, —O—(C=O)—$CH_3$, and —(C=O)—O—R. Further, any nitrogen atom may be optionally oxidized to the N-oxide, and any sulfur atom may be optionally oxidized to a sulfoxide.

Non-limiting examples of six-membered rings which are suitably selected for Q include, without limitation, 2H-pyran, tetrahydropyran, piperidine, 1,4-dioxane, morpholine, piperazine, 1,4-dithiane, thiomorpholine, pyridine, pyrazine, pyridazine, pyrimidine, 1,2,3-triazine, 1,2,4-triazine, 1,3,5-triazine, 1,2,3,4-tetrazine, and pentazine, to name a few. Q may be selected from, for example, the following six membered heterocyclic rings which are aromatic, fully saturated, or comprises one, two, or three double bonds:

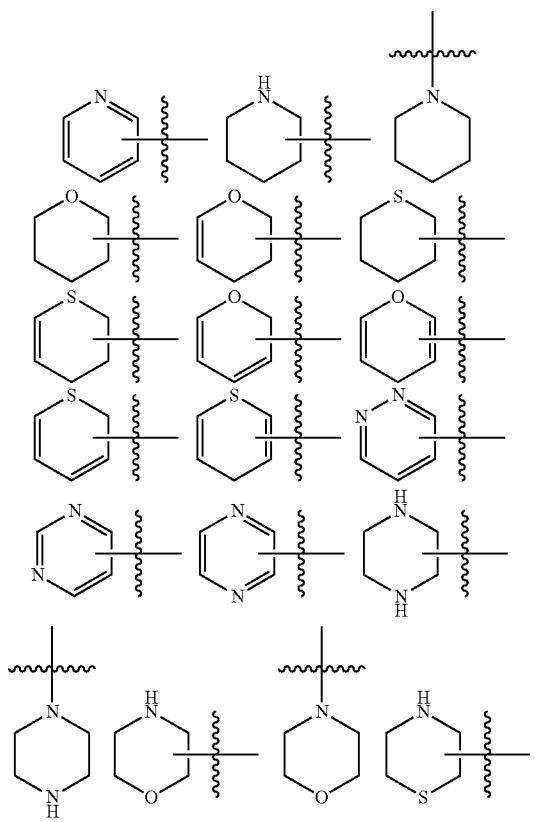

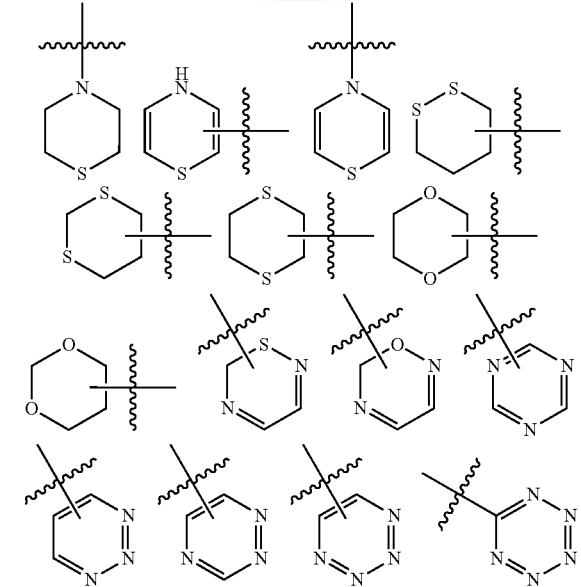

These six membered rings may be optionally functionalized with one or more groups R*, as defined above, with particular mention being made of $C_{1-4}$ alkyl (e.g., methyl, ethyl, isopropyl, etc.), $C_{1-4}$ alkoxyl, halo, hydroxyl, oxo, thiol, amino, alkylamino, dialkylamino, —$CH_2$—$N(CH_3)_2$, —$(CH_2)_{1-6}$—$N(R^N)_2$, —(C=O)—H, —(C=O)—R, —(C=O)—$CH_3$, —(C=O)—$CH_2CH_3$, —O—(C=O)—R, —O—(C=O)—$CH_3$, and —(C=O)—O—R. Further, any nitrogen atom may be optionally oxidized to the N-oxide, and any sulfur atom may be optionally oxidized to a sulfoxide.

In one embodiment, Q is phenyl and "n" is 1, 2, or 3. In one interesting embodiment, Q is phenyl, "n" is 1, and R* is a group —$(CH_2)_{1-6}$—$N(R^N)_2$, and in particular —$CH_2$—$N(CH_3)_2$. In this embodiment, R* may by para, meta, or ortho to the point of attachment to the pyridone ring, as illustrated in formula (III).

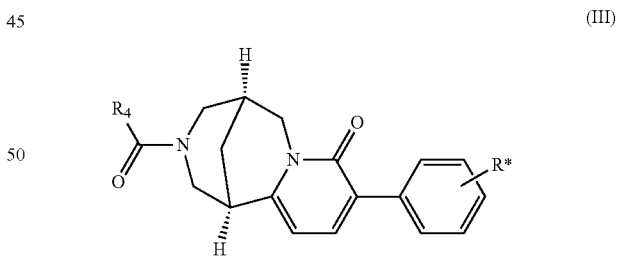

(III)

In this and all embodiments, R* and/or $R_4$ may be a lower ($C_1$-$C_6$) aliphatic group, including for example, methyl, ethyl, n-propyl, isopropyl, cyclopropyl, n-butyl, sec-butyl, iso-butyl, tert-butyl, cyclobutyl, 1-methylbutyl, 1,1-dimethylpropyl, n-pentyl, cyclopentyl, iso-pentyl, neo-pentyl, n-hexyl, and cyclohexyl, or the like. These lower alkyl group may also include 1-6 heteroatoms selected from O, S, and N in the chain or attached to the chain. Representative groups for R* and/or $R_4$ include, but are not limited to, —$(CH_2)_a$—$CH_3$ where "a" is an integer from 1 to 5, including, for example, —$CH_2$—$CH_3$, —$CH_2CH_2CH_3$, —$CH_2CH_2CH_2CH_3$, or —$CH_2CH_2CH_2CH_2CH_3$; linear alkoxy moieties of the general form —O(CH$_2$)$_a$—CH$_3$ where "a" is an integer from 1 to 5, including for example, —OCH$_2$CH$_3$, —OCH$_2$CH$_2$CH$_3$, or —OCH$_2$CH$_2$CH$_2$CH$_3$; groups of the form —O—(CH$_2$)$_a$—O—(CH$_2$)$_b$CH$_3$ where "a" and "b" are each independently integers from 1 to 4; —(CH$_2$)$_a$—O—(CH$_2$)$_b$CH$_3$ or —(CH$_2$)$_a$S(CH$_2$)$_b$CH$_3$, where "a" and "b" are each independently integers from 1 to 4; or a moiety of the form —(CH$_2$)$_b$NR$^N{}_2$ where R$^N$ is independently at each occurrence a group —(CH$_2$)$_c$CH$_3$ where "b" is an integer from 1 to 4 and "c" is an integer from 0 (zero) to 4. Specific examples of R* and/or R$_4$ include, without limitation, —O—CH$_3$, —O—CH$_2$CH$_3$, —O—CH$_2$CH$_2$CH$_3$, —CH$_2$—O—CH$_3$, —CH$_2$—O—CH$_2$CH$_3$, —CH$_2$CH$_2$—O—CH$_3$, —N(CH$_3$)$_2$, —N(CH$_2$CH$_3$)$_2$, —N(CH$_2$CH$_2$CH$_3$)$_2$, —S—CH$_3$, —S—CH$_2$CH$_3$, —CH$_2$—S—CH$_3$, —CH$_2$—S—CH$_2$CH$_3$, —CH$_2$CH$_2$—S—CH$_3$, —S—CH$_2$CH$_2$CH$_3$, —CH$_2$CH$_2$—S—CH$_3$, —CH$_2$—S—CH$_2$CH$_3$, —CH$_2$—N(CH$_3$)$_2$, —CH$_2$—N(CH$_2$CH$_3$)$_2$, —N(CH$_3$)$_2$, —N(CH$_2$CH$_3$)$_2$, —CH$_2$—N(CH$_2$CH$_2$CH$_3$)$_2$, —CH$_2$CH$_2$—N(CH$_3$)$_2$, and —CH$_2$—N(CH$_2$CH$_3$)$_2$, to name a few.

In one embodiment, R* is a group —(CH$_2$)$_{1-6}$—N(R$^N$)$_2$, and in particular —CH$_2$—N(CH$_3$)$_2$. In another embodiment, R$_4$ is a group —CH$_2$—S—CH$_3$. Excellent results have been obtained with the compounds according to formulas (IV-A) and (IV-B), shown below, where R* comprises a tertiary amine group ortho or para to the point of attachment to the pyridone ring and R$_4$ comprises a linear thioether moiety:

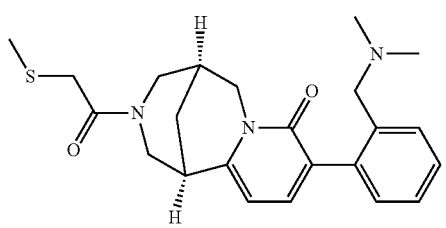
(IV-A)

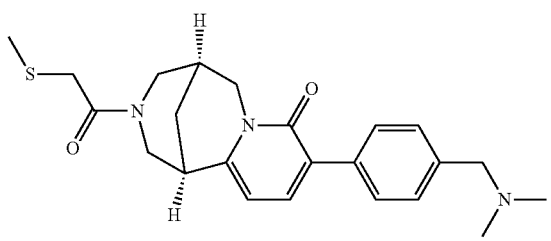
(IV-B)

In formulas (I)-(III), R$_4$ may, for example, also be a group a group -Q(-R)$_n$, where Q is, independent from R$_1$, any of the cyclic groups defined above. In some embodiments, R$_1$ and R$_4$ are, independently, a group -Q(—R)$_n$, where Q is the same or different at both occurrences. In one embodiment, R$_1$ is an optionally substituted five- or six-membered aromatic group, such as the five-membered furyl group, and R$_4$ is an optionally substituted five- or six-membered aromatic group, such as phenyl group. The compound according to formula (V), has been found useful:

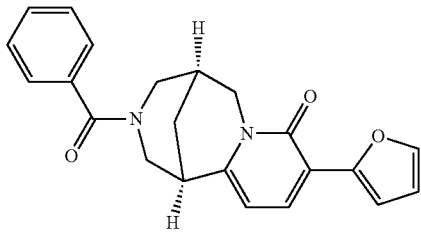
(V)

In addition to the paxillin-stimulating compounds according to formulae (I)-(V), other pyridone-fused azabicyclic compounds capable of stimulating paxillin are contemplated, including without limitation, those described in International Patent Application Publication WO 98/18798; EP 0 581 457; U.S. Pat. Nos. 6,630,467, 6,235,734, the disclosures of which are incorporated herein by reference in their entirety.

In some embodiments, the paxillin stimulator comprises another kind of organic molecule, such as, e.g., Tanshinone IIA; Tetrandrine; Carvacol; and/or cis-6-Nonenol, and/or salt thereof. Tanshinone IIA, or 1,6,6-trimethyl-8,9-dihydro-7H-naphtho[1,2-g][1]benzofuran-10,11-dione, is a diterpenoid naphthoquinone and an active component of some traditional Chinese medicines based on *Salvia miltiorrhiza*. It is believed to have anti-inflammatory activity and induces apoptosis in a variety of cell lines. H. J. Sung et al. Exp. Mol. Med. 1999 Vol. 31:174. It has also been suggested for use in treating sepsis, septicemia, and endotoxic shock. See, e.g., International Patent Application Publication WO 2007/084419, which is incorporated herein by reference in its entirety. Tanshinone IIA is commercially available, e.g., it can be obtained from Biomol Research Laboratories, PA.

Tetrandrine, or 6,6',7,12-Tetramethoxy-2,2'-dimethyl-berbaman, is a bis-coclaurine alkaloid, which has been used for centuries in Chinese traditional medicines, for example, for treating cardiovascular diseases. It is believed to be a calcium channel blocker as well as a blocker of the Ca$^{2+}$-activated potassium channels. Dworetzky et al. J. Neurosci. 1996. Vol. 16: 4543; and Gadwood et al. Annu Rep. Med. Chem. 1989 Vol. 24: 187. It is also commercially available, e.g., from Biomol Research Laboratories, PA.

Carvacrol, or cymophenol, C$_6$H$_3$CH$_3$(OH)(C$_3$H$_7$), is a monoterpenoid phenol, having a characteristic pungent, warm odor, similar to that of oregano, and is also known if its pizza-like taste. Ultee A. et al. (2000) J. Food Prot. 63 (5): 620-4. Carvacrol is present in oils of *Origanum vulgare*, thyme, pepperwort, and wild bergamot. It is known to inhibit growth of a number of bacteria strains and accordingly has been used as a food additive to prevent bacterial contamination. Ultee A. et al. (2001) Int. J. Food Microbiol. 64 (3): 373-8.

Cis-6-Nonenol is an unsaturated fatty alcohol. Cis-6-nonenol has the structure of formula (VI), shown below, and has been further described in U.S. patent application Ser. No. 12/342,197, filed Dec. 23, 2008, entitled "Topical Compositions Containing cis-6-Nonenol and its Derivatives and Methods for Treating Skin" incorporated herein by reference in its entirety.

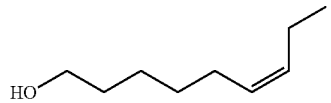
(VI)

In some embodiments, the paxillin stimulator comprises a larger organic molecule, such as, e.g., retinyl punicate; retinyl oleate; and/or Equol. Retinyl punicate and retinyl oleate are esters of retinol (vitamin A) with the fatty acids punicic acid and oleic acid, respectively. The esters can be obtained as known in the art, e.g., by esterification reaction. Retinyl oleate has been suggested for use in enhancing skin and for treating dermatological disorders, including acne, oily skin, and rosacea. See, e.g., EP 0 807 429, which is incorporated herein by reference in its entirety Equol, or 4',7-isoflavandiol, has been suggested for use in treating androgen-mediated pathologies of skin and hair, by blocking the hormonal action of 5-dihydrotestosterone. See, e.g., International Patent Application Publication WO 2005/107770, which is incorporated herein by reference in its entirety. It is an isoflavandiol and nonsteroidal estrogen, made by bacterial flora in the intestines of some individuals. Wang, X. L., et al. Applied and Environmental Microbiology (2005) 71:214-219; Frankenfeld, C. L. et al. The British journal of Nutrition (2005) 94:873-876.

In some embodiments, the paxillin stimulator comprises a biological extract, e.g., a plant extract. Extracts of plants useful as paxillin stimulators in the present invention include without limitation *Jasminum sambac* extract; *Coccinia grandis* extract; *Ecliptica prostrata* Linn. extract; *Clitoria ternatea* Linn. extract; *Ozothamnus obcordatus* extract; *Erythrina flabelliformis* extract; *Lonchocarpus capassa* extract; *Sophora tomentosa* extract; *Trifolium hybridum* extract; *Eremophila mitchellii* extract; *Kunzea ambigua* extract; *Zanthoxylum nitidium* extract; *Ophiopogon Thunb.* P.E. extract; *Radix platycodonis* extract; *Terminalia belerica* extract; *Cocculus glaucescens* extract; *Stephania* solid extract; and/or rosemary extract, preferably rosemary PE 50%.

*Jasminum sambac* is a species of jasmine native to southwestern and southern Asia, the Philippines, India, Myanmar and Sri Lanka. It produces strongly-scented flowers, used as ornaments, to make fragrant leis, and as the main ingredient in jasmine tea. *Coccinia grandis*, also known as ivy gourd, is a tropical vine grown in some parts of the world for its small edible fruits. The fruit is commonly eaten, e.g., in Indian cuisine, whereas the vine is considered an invasive plant in the United States and Hawai'i. *Coccinia grandis* has been suggested as useful in skin whitening applications, e.g., see JP 2000095663, which is incorporated herein by reference in its entirety. *Ecliptica prostrata* Linn., also known as False Daisy or bhringraj, grows as a week in moist places, including India, China, Brazil, and Thailand, and is used in many traditional medicines in those areas. For example, in Brazil it is used to treat snakebites and in India is it used to improve hair growth. Chopra, et al. 1955. Glossary of Indian Medicinal plants. C.S.I.R., New Delhi. Chinese traditional medicine applications for the plant include treating athlete's foot, eczema, and dermatitis. *Clitoria ternatea*, also known as Butterfly pea, is native to tropical and temperate areas, including southeast Asia. The flowers can be used as a food dye and extracts of the roots are considered in some cultures to have medicinal properties, such as treating whooping cough. *Ozothamnus obcordatus*, also known as Grey Everlasting, is a shrub native to some parts of Australia and is regarded as having commercial cut-flower potential.

*Erythrina flabelliformis*, also known as Coral Bean, is shrub bearing red flowers in showy clusters, as well as large pods with highly toxic red beans. It has been suggested for use in extractions to obtain useful chemicals from plants. See, e.g., U.S. Pat. Appl. Publ. No. 2002/0132021, which is incorporated herein by reference in its entirety. *Lonchocarpus capassa*, also known as apple-leaf or rain tree, is found in southern Africa. It is known for its smooth bare trunk with a high-branching sparse canopy. The tree is often infected with aphids, which excrete drippings to form wet patches beneath the tree, giving it the name "rain tree." *Sophora tomentosa*, also known as "necklace pod", is a shrub bearing yellow flowers and silver, velvety foliage. The plant is native to coastal areas of Florida and the Caribbean. *Trifolium hybridum*, also known as "alsike clover", is a plant in the pea family, bearing stalked, pale pink flowers, sometimes grown as fodder. Plant extracts have been used in dermatological applications, ostensibly as inhibitors of extracellular proteases. See, e.g., U.S. Pat. Appl. Publ. No. 2007/0122492, which is incorporated herein by reference in its entirety. *Eremophila mitchellii*, also known as "false sandalwood", is as shrub or small tree native to Australia that bears white or pale pinkish flowers. *Kunzea ambigua*, also known as "poverty bush", is a shrub found growing in sandstone soils of eastern Australia. It is used in gardening and sand dune stabilization. It has also been suggested for use in treating psoriasis. See, e.g., International Patent Application Publication WO 2009/086595, which is incorporated herein by reference in its entirety.

*Zanthoxylum nitidium* is a shrub known for the use of its roots and sometimes bark in traditional Chinese medicine. Several alkaloids thought to contribute to its medicinal qualities have been isolated from extracts of this plant. Mingjin L. et al. (2006) J. of Pharm. and Biomed. Anal. 42(2):178-183. *Ophiopogon Thunb.* is a grass-like shrub widely cultivated in China for its tuberous roots, which are used medicinally. Extracts can by obtained commercially, e.g., from Wuchang Yuancheng Technology Development Co., Ltd., China. *Radix platycodonis* is another plant used in traditional Chinese medicine. For example, its roots can be dried to form a brown powder that is available commercially, e.g., from Qi Lu Chemical, China. *Terminalia belerica*, also known as bibhitaka, is a tall tree growing throughout India with brownish grey bark and offensive-smelling flowers. In Sanskrit, babhitaka means something that keeps away disease, and parts of the tree are used extensively in traditional medicines. Extracts also have been suggested for use as de-pigmenting agents. See, e.g., International Patent Application Publication WO 96/24327, which is herein incorporated by reference in its entirety. *Cocculus glaucescens* is a large, woody vine used in traditional Chinese medicine. *Stephania* is a genus of flowering plants that grows as perennial vines native to eastern and southern Asia and Australia. Some species provide herbs used in traditional Chinese medicine and solid extracts of the plant parts, e.g., the roots are commercially available, e.g., from Natural Nutritionals, GA, as well as from Naturex, Inc, N.J., which provides an *Stephania* solid extract suitable for use in accordance with the invention. Rosemary, *Rosmarinus officinalis*, is a woody perennial herb with fragrant evergreen needle-like leaves, native to the Mediterranean region and extensively used in traditional Mediterranean cuisine. Rosemary extract suitable for use in the invention is commercially available, e.g., from Naturex, Inc., NJ.

In some embodiments, the paxillin stimulator comprises other biological materials, e.g., MycoFusions Coriolus Black Corn Biomass and/or MycoFusions Maitake Waxy Hulless Barley Biomass. MycoFusions Coriolus Black Corn Biomass and MycoFusions Maitake Waxy Hulless Barley Biomass are commercially available, e.g., from Nutragenesis, LLC, VT.

The cosmetic composition for topical application to the skin will comprise at least one paxillin stimulator in a cosmetically acceptable vehicle. The paxillin stimulator may be at least one substance selected from the group consisting of pyridone-fused azabicyclic compounds having the structure of formulae IV or V; *Jasminum sambac* extract; *Coccinia grandis* extract; *Eliptica prostrata* Linn. extract; *Clitoria ternatea* Linn. extract; *Ozothamnus obcordatus* extract; *Erythrina flabelliformis* extract; *Lonchocarpus capassa* extract; *Sophora tomentosa* extract; *Trifolium hybridum* extract; *Eremophila mitchellii* extract; *Kunzea ambigua* extract; Tanshinone IIA; Tetrandrine; Carvacrol; cis-6-Nonenol; Retinyl punicate; Retinyl oleate; Equol; MycoFusions Coriolus Black Corn Biomass; MycoFusions Maitake Waxy Hulless Barley Biomass; *Zanthoxylum nitidium* extract; *Ophiopogon Thunb*. P.E. extract; *Radix platycodonis* extract; *Terminalia belerica* extract; *Cocculus glaucescens* extract; *Stephania* solid extract; and Rosemary PE 50%. In some embodiments, the cosmetic composition comprises one or more paxillin stimulators, and in other embodiments, the cosmetic composition comprises two or more paxillin stimulators. In preferred embodiments, the combination of two or more paxillin stimulators produces synergistic effects, such as synergistically providing anti-aging benefits.

In some embodiments, the cosmetic composition for topical application to the skin comprises, in a cosmetically acceptable vehicle, cis-6-nonenol and at least one other paxillin stimulator in amounts effective to impart an anti-aging benefit to human skin. The paxillin stimulator may be at least one compound selected from the group consisting of pyridone-fused azabicyclic compounds having the structure of formulae IV or V; *Jasminum sambac* extract; *Coccinia grandis* extract; *Eliptica prostrata* Linn. extract; *Clitoria ternatea* Linn. extract; *Ozothamnus obcordatus* extract; *Erythrina flabelliformis* extract; *Lonchocarpus capassa* extract; *Sophora tomentosa* extract; *Trifolium hybridum* extract; *Eremophila mitchellii* extract; *Kunzea ambigua* extract; Tanshinone IIA; Tetrandrine; Carvacrol; Retinyl punicate; Retinyl oleate; Equol; MycoFusions Coriolus Black Corn Biomass; MycoFusions Maitake Waxy Hulless Barley Biomass; *Zanthoxylum nitidium* extract; *Ophiopogon Thunb*. P.E. extract; *Radix platycodonis* extract; *Terminalia belerica* extract; *Cocculus glaucescens* extract; *Stephania* solid extract; and Rosemary PE 50%. In some embodiments, the composition comprising cis-6-nonenol further comprises at least two, at least five, at least 8, at least 10, at least 15, at least 20, at least 25, or all 28 substances selected from the group recited above. In preferred embodiments, the combination of two or more paxillin stimulators produces synergistic effects, such as synergistically providing anti-aging benefits.

In some preferred embodiments, the cosmetic composition comprises at least one paxillin stimulator selected from the group consisting of pyridone-fused azabicyclic compounds having the structure of formulae IV or V; *Jasminum sambac* extract; *Eliptica prostrata* Linn. extract; *Clitoria ternatea* Linn. extract; *Ozothamnus obcordatus* extract; *Erythrina flabelliformis* extract; *Lonchocarpus capassa* extract; *Sophora tomentosa* extract; Tetrandrine; Carvacrol; Retinyl punicate; MycoFusions Coriolus Black Corn Biomass; MycoFusions Maitake Waxy Hulless Barley Biomass; *Zanthoxylum nitidium* extract; *Ophiopogon Thunb*. P.E. extract; *Radix platycodonis* extract; and *Cocculus glaucescens* extract. In some preferred embodiments, the paxillin stimulator comprises one or more of *Trifolium hybridum* extract, *Kunzea ambigua* extract, Tanshinone IIA, Equol, *Terminalia belerica* extract, or Rosemary extract. In some embodiments, one of more of *Trifolium hybridum* extract, *Kunzea ambigua* extract, Tanshinone IIA, Equol, *Terminalia belerica* extract, and Rosemary extract is used in combination with cis-6-nonenol to impart anti-aging benefit to skin.

In some preferred embodiments, one of more of the substances are excluded from the cosmetic composition. For example, in some embodiments, the composition does not include *Trifolium hybridum* extract and/or does not include retinyl oleate and/or does not include Equol.

Cosmetic compositions of the instant invention generally comprise an amount of a paxillin stimulator, e.g., an amount of cis-6-nonenol, effective to provide a benefit to human skin. In preferred embodiments, the compositions comprise an amount of a paxillin stimulator effective to increase paxillin transcription and/or expression in human dermal fibroblasts. Cosmetic compositions described herein find use as anti-aging agents, e.g., as detailed below.

Cosmetic Use of Paxillin Stimulating Compositions

Another aspect of the instant invention relates to cosmetic use of compositions comprising a paxillin stimulator, such as cis-6-Nonenol. The cosmetic compositions surprisingly act to increase paxillin levels in human dermal fibroblasts and accordingly find use in anti-aging products.

In some embodiments, a method for providing at least one benefit to human skin is provided, where the method comprises topically applying to skin in need thereof at least one paxillin stimulator in a cosmetically acceptable vehicle. The composition will comprise an effective amount of the substance. An "amount effective" or an "effective amount" to provide a particular benefit to the skin refers to the active amount of a paxillin stimulator sufficient to provide a clinically measurable improvement in the particular manifestation of skin when applied for a sufficient time. "Amounts effective" or "effective amounts" to provide a particular benefit to the skin refers to the active amounts of each of two or more paxillin stimulators used in combination to provide a clinically measurable improvement in the particular manifestation of skin when applied for a sufficient time. The effective amount of each substance when used in combination with another may be the same, greater than, or less than the effective amount of the substance when used alone. Use of lower amounts of individual substances is contemplated when used in combination with other paxillin stimulators, e.g., due to synergistic effects in producing a clinically measurable improvement in a particular manifestation of skin. Such benefits include without limitation, the following:

(a) treatment, reduction, and/or prevention of fine lines or wrinkles, (b) reduction of skin pore size, (c) improvement in skin thickness, plumpness, and/or tautness;

(d) improvement in skin suppleness and/or softness;

(e) improvement in skin tone, radiance, and/or clarity;

(f) improvement in procollagen and/or collagen production;

(g) improvement in skin texture and/or promotion of retexturization;

(h) improvement in skin barrier repair and/or function;

(i) treatment and/or prevention of skin sagging or atrophy; and/or (j) improvement in appearance of skin contours;

(k) restoration of skin luster and/or brightness;

(l) replenishment of essential nutrients and/or constituents in the skin;

(m) improvement of skin appearance decreased by menopause;

(n) improvement in skin moisturization and/or hydration; and (o) improvement of skin elasticity and/or resiliency.

The compositions of the invention can be applied to skin in need of treatment, such as skin which suffers from a deficiency or loss in any of the foregoing attributes or conditions, or which would otherwise benefit from the composition's anti-aging effects, e.g., as described herein. For example, the paxillin stimulator(s) can be provided in a cosmetically acceptable vehicle, topically applied to a desired area of skin, and allowed to remain on the area in amount effective(s) to treat and/or prevent an unwanted feature or condition of the skin, and/or to improve the aesthetic appearance of the skin.

"Condition of the skin" or "skin condition" is used interchangeably herein with "skin disorder." "Treatment" as used herein, as well as related terms such as "treat" or "treating," refers to eradicating, reducing, ameliorating, or reversing one or more of the unwanted features associated with the skin condition being treated, such that the consumer perceives an improvement or other treatment benefit with respect to the condition. "Prevention" as used herein, as well as related terms such as "prevent" or "preventing," refers to affording skin not yet affected by the condition a benefit that serves to avoid, delay, forestall, or minimize one or more unwanted features associated with the skin condition to be prevented. Such preventative benefits include, for example, delaying development of the condition, or reducing the duration, severity, or intensity of one or more unwanted features associated with the condition if it eventually develops.

Anti-Aging Benefits

In certain preferred embodiments, the cosmetic compositions described herein can be used to treat and/or prevent signs of skin aging or other skin damage (e.g., from UV). Signs of skin aging include any dermatological signs of aging, including signs caused by intrinsic (chronological) aging, or caused by extrinsic factors (such as in photoaging). The compositions may be applied to skin already showing visible signs of aging, or likely to show such signs, e.g., due to age or sun exposure.

An early sign of skin aging involves the gradual development of facial wrinkles, whether fine surface lines or deeper creases and folds. While wrinkling and other signs of aging are intrinsic to skin, the process may be accelerated by external factors, such as excessive exposure to the sun and other damaging elements, overactive facial expression muscles, frequent use of tobacco products, poor nutrition, or certain skin disorders. Fine surface lines that progress to deeper creases, deepening facial wrinkles due to repeated skin folding, and deep folds that develop with maturity are visible changes associated with aging.

Treating signs of skin aging refers to eradicating, reducing, ameliorating, or reversing one or more of the unwanted features associated with skin aging, e.g., by reducing lines and/or wrinkles a perceptible extent. For example, compositions and methods of the instant invention may be used to reverse or treat signs of skin aging once manifested, such as is common in individuals over 25 years of age. Preventing signs of skin aging refers to affording skin a benefit that serves to avoid, delay, forestall, or minimize one or more unwanted features associated with aging, e.g., by slowing the appearance of lines and/or wrinkles as the skin eventually ages. That is, the compositions and methods of the instant invention may be employed prophylactically, e.g., to forestall signs of skin aging in individuals that have not yet manifested signs of skin aging, most commonly in individuals under 25 years of age.

The improvement in the unwanted feature and/or overall aesthetic appearance can include one or more of the following: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing skin atrophy; improving skin tone, radiance, and/or clarity; preventing, reducing, and/or ameliorating skin sagging; improving skin firmness, plumpness, tautness, suppleness and/or softness; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause, such as essential nutrients or other skin constituents; ameliorating the effects of estrogen imbalance; improving communication among skin cells; increasing cell proliferation and/or multiplication; increasing skin cell metabolism decreased by aging and/or menopause; retarding cellular aging; improving skin moisturization and/or hydration; improving production and/or reducing loss of collagen and/or pro-collagen; enhancing skin thickness; increasing skin elasticity and/or resiliency; and any combinations thereof. Without wishing to be bound by theory, it is believed that the compositions of the present invention enhance and improve the aesthetic appearance of skin by enhancing paxillin expression and increasing paxillin levels in dermal fibroblasts.

In certain preferred embodiments, the compositions and methods of the invention are directed to the treatment and/or prevention of fine lines or wrinkles in the skin. In the case of treatment, the compositions are applied to skin in need of such treatment, by which is meant skin having wrinkles and/or fine lines. The fine lines and/or wrinkles may occur on any surface of the skin, including without limitation, the skin of the hands, arms, legs, neck, chest, and face, including the forehead. Preferably, the compositions are applied directly to the fine lines and/or wrinkles. For example, methods for treating fine lines and wrinkles may comprise topically applying a composition described herein to skin of an individual in need thereof, e.g., topically applying directly to a fine line and/or wrinkle in an amount and for a time sufficient to reduce the severity of the fine lines and/or wrinkles; or to inhibit formation of new lines and/or wrinkles. The effect of a composition on the appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

The term "wrinkle" or "wrinkling" refers to both fine wrinkling and/or coarse wrinkling Fine wrinkling or fine lines refers to superficial lines and wrinkles on the skin surface. Coarse wrinkling refers to deep furrows, particularly deep lines/wrinkles on the face and around the eyes, including expression lines such as frown lines and wrinkles, forehead lines and wrinkles, crow's feet lines and wrinkles, nasolabial folds, and marionette lines and wrinkles Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth.

It is also contemplated that the compositions of the invention will be useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or post-menopausal, as it is believed that skin thins differently with age in men and women, and in particular in women at different stages of life.

Without wishing to be bound by theory, it is believed that compounds described herein can act to increase paxillin levels in dermal fibroblasts, thereby maintaining cell shape and health, and delaying one or more of the unwanted features associated with skin aging. It has surprisingly been found that in human skin fibroblasts, paxillin protein levels decrease with aging. For example, dermal fibroblasts from older donors showed 20.6% lower paxillin levels compared to younger donors (n=3). Furthermore, interference of the normal production of paxillin mRNA and protein directly lead to changes in cell shape of human skin fibroblasts. Collapsed fibroblast have a lower rate of proliferation and reduced ability to produce collagen matrix Accordingly, increasing paxillin levels can maintain youthful skin cell morphology and hence cellular function, including retarding cellular aging and stimulating collagen synthesis. More youthful paxillin levels may improve and/or restore skin cell shape, increase cell proliferation and production of extra-cellular matrix proteins, hence leading to overall healthier skin with fewer lines and wrinkles.

In certain preferred embodiments, the compositions and methods of the instant invention are directed to improving skin firmness, plumpness, and/or tautness. Loss of firmness, wrinkling and other signs of aging result in part from loss of skin collagen over time. As used herein "collagen" is used interchangeably with "collagen I" or "collagen type I," the type present in skin as a dermal matrix component. Collagen I is composed of three protein chains wound together in a tight triple helix, which provides a tensile strength greater than that of steel and is created by fibroblasts. Collagen gives skin firmness, strength, durability, and a youthful, smooth, plump appearance. Without wishing to be bound by theory, it is believed increasing paxillin levels can lead to increased collagen production and thus collagen skin levels, thereby delaying one or more of the unwanted features associated with skin aging, e.g., by instead maintaining skin firmness and plumpness.

In certain embodiments, the compositions of the instant invention comprise a paxillin stimulator, such as cis-6-Nonenol, in an amount sufficient to increase paxillin level in a given area of skin when topically applied thereto. As used herein, "increasing paxillin level" and related expressions refer to stimulating, inducing, or up-regulating paxillin mRNA (and protein) production to increase the paxillin content in an area of skin, preferably improving skin appearance to a perceptible extent. For example, in some embodiments, the paxillin level is increased by at least about 10%, at least about 20%, at least about 60%, at least about 80%, at least about 100%, at least about 150%, at least about 200%, at least about 250%, or at least about 300%, compared to the level of paxillin in the absence of the composition. Paxillin levels in the skin can be determined by appropriate assays, e.g., in vitro assays described herein or known in the art. For example, Example 1 below provides experimental details of assays for measuring paxillin levels in human dermal fibroblasts.

In some embodiments, the cosmetic compositions for treating and/or preventing signs of skin aging can further comprise additional anti-aging agents. For example, the cosmetic composition comprising a paxillin stimulator (or paxillin stimulators) in an amount effective (or amounts effective) to treat and/or prevent signs of skin aging may further comprise at least one other anti-aging agent. It is contemplated that synergistic improvements may be obtained with such combinations, in some embodiments.

Exemplary anti-aging agents include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; antioxidants, exfoliating agents (e.g., glycolic acid, 3,6,9-trioxaundecane-dioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; elastase inhibitors; anti-aging botanicals, keratolytic agents, desquamating agents, keratinocyte proliferation enhancers, and skin plumpers that serve as additional collagen enhancers to the skin, to name a few. An example of a suitable skin plumper is palmitoyl oligopeptide. Other skin plumpers include other collagen and/or other glycosaminoglycan (GAG) enhancing agents. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof. In some embodiments, the invention relates to synergistic action of one or more compositions described herein with TDPA, e.g., to provide enhanced anti-aging benefits to skin.

Based on the teachings provided herein, one of skill in the art will recognize other cosmetic and/or pharmaceutical applications for the compositions described herein, and such applications are also contemplated as within the scope of the instant invention. For example, compositions described herein may also find use in personal care products, such as skin care products, where it is desirable to produce a skin benefit described herein upon application of the product. Personal care products for the skin include, for example, body lotions, body washes, body tonics, and the like. It is contemplated, for example, that compositions described herein can find use in lotion, tonic, and/or wash formulations that decrease the appearance of lines and wrinkles on various surfaces of the body.

The paxillin stimulator is topically applied to an individual in need thereof, by which is meant an individual standing to benefit from reducing visible signs of skin damage or aging. The invention provides methods for providing a skin benefit by topically applying a composition comprising at least one paxillin stimulator over an area of skin for a period of time sufficient to produce one or more of the benefits described herein. The composition will typically be applied to the skin one, two, or three times daily for as long as is necessary to achieve desired results, such as anti-aging benefits described herein. This treatment regiment may comprise daily application or every-other-day application for at least about one week, at least about two weeks, at least about four weeks, at least about eight weeks, at least about twelve weeks, or more. Chronic treatment regimens are also contemplated, e.g., with respect to prophylactic treatments aimed at forestalling one or more signs of skin aging or other damage. The treatment and/or prophylactic regime may also depend on specific the paxillin stimulator(s) being used, e.g., as certain paxillin stimulators may produce anti-aging skin benefits more quickly than others.

Additional candidate paxillin stimulators for use as anti-aging agents may be screened for use in treating skin in need thereof, e.g., as described in more detail below.

Methods for Screening Candidate Paxillin Stimulators

Still another aspect of the instant invention relates to screening candidate paxillin stimulators, e.g., to find substances suitable for formulating an anti-aging cosmetic composition by incorporation into a cosmetically acceptable vehicle. A vast array of substances can be screened and it should be understood, although not always explicitly stated, that a candidate paxillin stimulator may be used alone or in combination with another paxillin stimulator.

In some embodiments, the candidate agents encompass natural, synthetic or semi-synthetic organic compounds based on various core structures. The agent may encompass one or more numerous chemical classes, preferably comprising functional groups necessary for structural interaction with proteins, particularly hydrogen bonding, e.g., typically including at least an amine, carbonyl, hydroxyl or carboxyl group, and frequently at least two of the functional chemical groups. Candidate agents are also found among biomolecules including, but not limited to peptides, saccharides, fatty acids, steroids, purines, pyrimidines, benzodiazapines, derivatives, structural analogs, polynucleotides, macromolecular complexes, or combinations thereof.

Candidate agents may be obtained from a wide variety of sources including libraries of synthetic or natural compounds. In some embodiments, the candidate paxillin stimulator may be any organic or inorganic compound and a number of natural and/or synthetic libraries of compounds can be used to provide candidate agents. See, e.g., NCI Open Synthetic Compound Collection library, Bethesda, Md.; Pirrung et al., 2008, "Synthetic Libraries of Fungal Natural Products" ChemInform 39:2; Shang et al., 2005, "Advancing chemistry and biology through diversity-oriented synthesis of natural product-like libraries" Curr. Opin. Chem. Biol. 9:248-58; Webb T R, 2005, "Current directions in the evolution of compound libraries" Curr. Opin. Drug Discov. Devel. 8:303-8; Fodor et al., 1991, Science 251:767-73; Medynski, 1994, BioTechnology 12:709-710; Ohlmeyer et al., 1993, Proc. Natl. Acad. Sci. USA 90:10922-26; Erb et al., 1994, Proc. Natl. Acad. Sci. USA 91:11422-26; Jayawickreme et al., 1994, Proc. Natl. Acad. Sci. USA 91:1614-18; and Salmon et al., 1993, Proc. Natl. Acad. Sci. USA 90:11708-712).

Further, numerous means are available for random and directed synthesis of a wide variety of organic compounds and biomolecules, including expression of randomized oligonucleotides and oligopeptides. Alternatively, libraries of natural compounds in the form of bacterial, fungal, plant, and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents may also include cell lysates or sub-cellular compartments, extracts of plant or animal origin, or any combinations thereof.

The candidate agent may be assayed to determine whether it can stimulate paxillin by any means known in the art and/or described herein. For example, Example 1 below describes an assay for screening for candidate paxillin stimulators by testing for increase in paxillin mRNA. In some embodiments, the method involves contacting a human skin cell with the candidate agent or candidate material and assaying for up-regulation of paxillin mRNA. The concentration of candidate agent in a test sample will vary depending on the nature of the agent. For example, the candidate agent can be tested at one or more concentrations, e.g., at about 5%, at about 2%, about 1%, 0.1%, about 0.05%, about 0.01%, about 0.001%, about 0.0001%, about 0.00001%, about 0.000001%, and the like.

In some preferred embodiments, up-regulation of paxillin mRNA is assayed using a multiplex assay that employs a branched DNA technology. This technology is a hybridization-based method of target-specific RNA quantification that amplifies a signal(s) rather than target RNA, using labelled DNA probes. Probes for paxillin have been designed and synthesized. The probes preferably cover the target sequence to be identified. That is, the probes can be designed such that the nucleotide sequence corresponding to paxillin mRNA is covered or substantially covered by complementary sequences of the various probes. The probes generally include capture extenders (CE), label extenders (LE), and blockers (BL). Capture extenders are short sequences that bind the RNA to the beads used, e.g., beads commercially available from Luminex. Label extenders are short sequences that bind the RNA to DNA oligomers used in amplification (bDNA amplification oligos, which also may be referred to as PreAmplifier, Amplifier, or Label Probes). Blockers are short sequences that bind to RNA at regions within the target sequence that are not covered by the CE or the LE. This arrangement provides a target sequence that that is double-stranded, as the target sequence is covered (or substantially covered) by the combination of various probes directed to different regions of the target. Without wishing to be bound by theory, it is believed that providing a double-stranded target sequence improves specificity and/or sensitivity of the assay, for example, by improving hybridization efficiency.

In one embodiment, CE, LE, and BL sequences for identifying paxillin correspond to SEQ ID NOS: 1, 2, and 3, respectively, as set forth below:

```
                                              (SEQ ID NO: 1)
gggaagacgtggcaccctcccggaacttcttcgagcccgcgctgctac tactgcaacggccccatcctggaagccttctttggtcccgaaaacggcag cttcttcgagc;
```

-continued (SEQ ID NO: 2)
gagcacttcgtctgcacccactgccaggaggagatcggataaagtggtga cagcccttgaccggacgtggcaccctgagggttccacgagaaggacggca aggcctactgtcgcaagtgctttgtgtgccgggaatgcttcacgccattc gtgacgacgggcagccctactgtgaggtgcactaccacgagc;
and (SEQ ID NO: 3)
acacttcttctgtgcacagtgtggggactacttcgacatgttcgcaccca agtgtggcggctgcgcccgggccatcctggagaactatatctcagccctc aacacgctgtggcatcctga.

In other embodiments, the probes used may comprise one or more variations from the above-recited sequences. For example, in some embodiments, the CE, LE, and/or BL probe has a nucleotide sequence that is at least about 70%, at least about 75%, at least about 80%, at least about 85%, at least about 90%, at least about 95%, or at least about 99% identical to the nucleotide sequence of SEQ ID NOS: 1, 2, and 3, respectively. In some embodiments, the CE, LE, and/or BL probe has a nucleotide sequence that hybridizes under stringent conditions to a nucleotide sequence of SEQ ID NOS: 1, 2, and 3, respectively. Stringent conditions can include conditions of low stringency, moderate stringency, or high stringency.

"High stringency conditions" can include, but are not limited to, those that (1) employ low ionic strength and high temperature for washing, for example 0.015 M sodium chloride/0.0015 M sodium citrate/0.1% sodium dodecyl sulfate at 50° C.; (2) employ, during hybridization, a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals©, 1987-1997, Current Protocols©, 1994-1997 John Wiley and Sons, Inc.; see also, Dyson, 1991, "Immobilization of nucleic acids and hybridization analysis," In: Essential Molecular Biology: A Practical Approach, Vol. 2, T. A. Brown, ed., pp. 111-156, IRL Press at Oxford University Press, Oxford, UK) (each of which is hereby incorporated by reference herein in its entirety).

"Moderately stringent conditions" are described by, but not limited to, those in Sambrook et al., Molecular Cloning: A Laboratory Manual. 2.sup.nd Ed., New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C.

"Low stringency conditions" can include, but are not limited to, the following. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). (see also Shilo and Weinberg, 1981, Proc. Natl. Acad. Sci. U.S.A. 78, 6789-6792).

Assay methods using the labelled probes involve capturing the target sequence and identifying captured sequences using one or more signal amplification steps. In some embodiments, appropriately diluted cell lysates are hybridized with paxillin and reference probes. Once the paxillin and the reference mRNAs are captured, the unbound material can filtered and washed. Signal amplification can be performed in one or more steps, typically in two steps using a "Pre-amplifier" probe, followed by an "Amplifier" probe, where unbound Pre-amplifier is filtered and washed before amplification with the Amplifier. The samples then can be hybridized with a labelled probe, filtered and washed as before, and finally, the labels read or measured.

Increase in paxillin level may be measured as a percent increase relative to a control. Preferred paxillin stimulators increase paxillin levels by at least about 60%, at least about 80%, at least about 100%, at least about 150%, at least about 200%, at least about 250%, or at least about 300%, compared to the level of paxillin in the absence of the composition or to that in the presence of a control. A candidate material thus can be identified as a paxillin stimulator, e.g., a candidate material can be identified as up-regulating paxillin mRNA using one or more probes, compositions, and/or methods described herein, and such identified candidate materials are encompassed within the scope of the instant invention.

Identified paxillin stimulators may be used to formulate cosmetic compositions, as known in the art. The cosmetic compositions find use in anti-aging products, preferably formulated for topical application to the skin e.g., with a cosmetically acceptable vehicle. Formulations for anti-aging cosmetic products comprising paxillin stimulators are described in more detail below.

Cosmetic Formulations of Paxillin Stimulating Compounds

The compositions according to the invention can be formulated in a variety of forms for topical application and will comprise from about 0.000001% to about 5% by weight of paxillin stimulator, from about 0.00001% to about 2% by weight of paxillin stimulator, and preferably will comprise from about 0.0001% to about 1% by weight, more preferably from about 0.001% to about 0.1% by weight, and even more preferably 0.01% to about 0.05% by weight based on the total weight of the composition. The above amounts refer to an "active amount" of the paxillin stimulator, such as the amount of cis-6-nonenol. The term "active amount" refers to the amount of paxillin stimulator absent diluent, solvent, carrier, filler or the like. The compositions will comprise effective amount(s) of paxillin stimulator(s), by which is generally meant amount(s) sufficient to increase paxllin mRNA and/or protein levels in given area of skin when topically applied thereto for a sufficient period of time.

In some embodiments, the cosmetic composition includes cis-6-Nonenol and optionally at least one other paxillin stimulator. In some such embodiments, the composition is essentially free of the trans-6-nonenol isomer or essentially free of nonenol isomers having the double bond in positions other than the 6-position. By "essentially free of" is meant that such other nonenol constituents will comprise less than 5% by weight of the total amount of nonenol, preferably, less than 2.5% by weight, and more preferably, less than 1% by weight. In other embodiments, the compositions will be free of nonenols other than cis-6-Nonenol.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The compositions can include a cosmetically acceptable vehicle, encompassing any pharmaceutically, physiologically or dermatologically-acceptable vehicle, diluent or carrier. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol phase, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions, or the like having the appearance of a cream, gel or microemulsions. The emulsion may include an emulsifier, such as a nonionic, anionic or amphoteric surfactant.

The oil phase of the emulsion preferably has one or more organic compounds, including emollients; humectants (such as butylene glycol, propylene glycol, Methyl gluceth-20, and glycerin); other water-dispersible or water-soluble components including thickeners such as Veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystaline wax, silicone waxes, fluorinated waxes, and any combination thereof.

Non-limiting emulsifiers included emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. The preferred emulsifiers include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: sorbitan esters; polyglyceryl-3-diisostearate; $C_{10-30}$ alkyl acrylate crosspolymer; Dimethicone PEG-7 isostearate, acrylamide copolymer; mineral oil; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, from about 0.1% to about 3% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)$_m$— and/or -(PO)$_n$— groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

In certain embodiments, the composition may comprise up to about 70% by weight of volatile solvent(s), including volatile organic solvents. Specifically, the composition may comprise up to about 60%, preferably up to about 50%, more preferably up to about 40%, and even more preferably up to about 30% by weight of volatile solvent(s). In other embodiments, the composition may be free of volatile solvents, including volatile organic solvents.

The compositions may include liposomes. The liposomes may comprise other additives or substances and/or may be modified to more specifically reach or remain at a site following administration.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives (e.g., DMDM Hydantoin/Iodopropynylbutylcarbonate), stabilizers, pharmaceutical agents, photostabilizing agents, neutralizers (e.g., triethanolamine) and mixtures thereof. In addition to the foregoing, the cosmetic compositions of the invention may contain any other compound for the treatment of skin disorders.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions of the invention may include a fragrance. Fragrances are substances which can impart an aesthetically pleasing aroma to the composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the composition in an amount ranging from about 0.001 to about 5 weight percent, preferably about 0.01 to about 0.5 percent by weight. Fragrance may also be imparted to the composition by the paxillin stimulator, e.g., where the paxillin stimulator comprises a plant extract having a pleasant or desirable aroma. In other embodiments, the compositions of the invention will be fragrance-free, by which is meant that the composition will not contain fragrances, in particular components that are added for the primary benefit of providing aroma.

The present compositions may also contain one or more insect repellent actives. Such actives include, but are not limited to, N,N diethyl-m-toluamide (DEET), ethyl butylacetylaminopropionate (IR3535 by Merck Co.), hydroxyethyl isobutyl piperidine carboxylate (1-piperidine carboxylic acid) (Bayer KBR 3023), p-menthane-3,8-diol, oil of citronella, soy bean oil, lemon grass oil, geranium/geraniol oil, neem oil and other natural essential oils, p-menthane-3,8-diol, or any mixtures thereof. The insect repellent active may be present in an amount about 0.05 wt % to about 90 wt %, preferably about 0.1 wt % to about 50 wt %, and most preferably about 0.1 wt % to about 30 wt %, based on the total weight of the composition. In other embodiments, the compositions of the invention will be free of an insect repellent active, by which is meant that the composition will not contain insect repellents, e.g., components that are typically added for the primary benefit of repelling insects.

In one embodiment of the invention, the compositions may include additional skin actives such as, but are not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, advanced glycation end-product (AGE) inhibitors and alpha-hydroxyacids.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Anogeissus latifolia, Asmunda japonica, Azadirachta indica, Butea frondosa, Butea monosperma, Cedrus deodara, Emblica officinalis, Ficus benghalensis, Glycyrrhiza glabra, Ilex purpurea Hassk, Innula racemosa, Ligusticum chiangxiong, Ligusticum lucidum, Mallotus philippinensis, Mimusops elengi, Morinda citrifolia, Moringa oleifera, Naringi crenulata, Nerium indicum, Psoralea corylifolia, Stenoloma chusana, Terminalia bellerica*, tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors, to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles Examples include isopropyl myristate, petrolatum, isopropyl lanolate, silicones (e.g., methicone, dimethicone), oils, mineral oils, fatty acid esters, cetyl ethylhexanoate, $C_{12-15}$ alkyl benzoate, isopropyl isostearate, diisopropyl dimer dillinoeate, or any mixtures thereof. The emollient may be preferably present from about 0.1 wt % to about 50 wt % of the total weight of the composition.

A skin plumper serves as an additional collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

It is preferred that the composition be essentially free of components having a strong oxidizing potential, including for example, organic or inorganic peroxides. By "essentially free of" these components is meant that the amounts present are insufficient to have a measurable impact on the beneficial activity of the paxillin stimulator(s). In some embodiments, this will be on a molar basis in relation to the amount of the paxillin stimulator(s), less than 1%.

In one embodiment, the composition of the invention comprising at least one paxillin stimulator may have a pH between about 1 and about 8. In certain embodiments, the pH of the composition will be acidic, i.e., less than 7.0, and preferably will be between about 2 and about 7, more preferably between about 3.5 and about 5.5.

All terms used herein are intended to have their ordinary meaning unless otherwise provided.

As used herein, "% by weight" or "% wt" refers to the weight percent of a component in relation to the total weight of the composition (i.e., including any carriers, vehicles, solvents, emollients, fillers, or other components added before application to the skin) unless otherwise specified.

EXAMPLES

Example 1: Stimulation of Paxillin mRNA In Vitro

Normal human dermal fibroblasts (Cascade Biologics) were cultured in 96-well tissue culture treated plates, with 200 µl DMEM in 10% serum per well, and incubated for 24 hours at 37° C. and 10% $CO_2$. In some cases, normal human epidermal keratinocytes (Cascade Biologics) were cultured in 200 µl EpiLife medium (Cascade Biologics) per well, and incubated overnight at 37° C. and 5% $CO_2$.

Stock solutions of candidate paxillin stimulators (test materials) were made in appropriate solvents (e.g., DMSO, water, ethanol, a 50:50 ethanol:water mixture) to give weight % as indicated in Table 1 below. Cells were treated with test material or a respective vehicle control diluted in growth medium for 24 hours in a humidified 37° C. incubator with 10% $CO_2$. After incubation, growth medium from each plate was removed and 100 µl of lysis buffer was added to the wells and placed in 37° C. incubator with 5% $CO_2$ for 30 minutes. At the end of incubation, the cells were collected in freezer plates and placed in a −80° C. freezer until analysis.

Changes in mRNA for paxillin in cell lysates after treatment were analysed using QuantiGene® multiplex assay (Panomics Inc. CA) that employs a branched DNA technology. This technology is a hybridization-based method of target-specific RNA quantification that amplifies a signal(s) rather than target RNA, using labelled DNA probe. Probes for Paxillin gene (ID: NM_005953) were designed and synthesized. Paxillin probes, reference probes PPIB and GAPDH, along with a set of other probes were used in this multiplex assay.

The probes used include capture extenders (CE), label extenders (LE), and blockers (BL). As described above, this arrangement provides a target sequence that is double-stranded, thereby improving hybridization efficiency. The CE, LE, and BL sequences used for identifying paxillin mRNA corresponded to SEQ ID NOS: 1, 2, and 3, respectively.

Appropriately diluted cell lysates were hybridized with the paxillin and reference probes in a hybridization plate in a Vortemp shaking incubator, for 18-22 hours at 54° C.±1° C. and 600 rpm. Once the paxillin and the reference mRNAs were captured, the unbound material was filtered using filter plates and washed three times with a wash buffer. Signal amplification was performed using two steps—first a 2.0 Pre-amplifier (Panomics Inc.) was added and incubated for 1 hour in the Vortemp shaking incubator at 54° C.±1° C. and 600 rpm. Unbound Pre-amplifier was filtered using a Filter plate and washed twice. Next the samples were exposed to 2.0 Amplifier (Panomics Inc.) and incubated, filtered, and washed as with the Pre-amplifier. Next the samples were hybridized with biotinylated labelled probe, and incubated for one hour at 54° C.±1° C. and 600 rpm. Samples were then filtered and washed as above. Finally, Streptavidin-conjugated Phycoerythrin (SAPE) working reagent was added and the mixture shaken for 30 minutes at room temperature covered in aluminium foil. Unbound SAPE was filtered and washed twice. SAPE wash buffer was added to each well with shaking for 2-5 minutes, and then readings were taken immediately using a Luminex machine.

Values for amounts of paxillin mRNA were determined along with those for the reference genes PPIB and GAPDH. Values were normalized to GAPDH to determine changes in paxillin mRNA after treatment. Percent increase in mRNA for paxillin was calculated in each case by comparing values after treatment with a candidate paxillin stimulator to values after treatment with the vehicle control.

Results for exemplary paxillin stimulators are presented below in Table 1.

TABLE 1

| Paxillin Stimulator | Weight % | % increase in Paxillin (relative to control) |
|---|---|---|
| Compound of Formula IV | 0.00005% | 31.67% |
| Compound of Formula V | 0.00005% | 28.52% |
| Jasminium sambac extract | 0.001% | 73.77% |
| Coccinia grandis extract | 0.10% | 73.12% |
| Eliptica prostrata Linn. extract | 0.10% | 102.2% |
| Clitoria ternatea Linn. extract | 0.10% | 54.0% |
|  | 0.01% | 57.1% |
| Ozothamnus obcordatus extract | 0.01% | 21.55% |
| Erythrina flab elliformis extract | 0.001% | 33.23% |
| Lonchocarpus capassa extract | 0.01% | 24.94% |
| Sophora tomentosa extract | 0.01% | 136.13% |
| Trifolium hybridum extract | 0.01% | 239.06% |
| Eremophila mitchelli extract | 0.01% | 138.34% |
| Kunzea ambigua extract 1 | 0.01% | 132.51% |
| Kunzea ambigua extract 2 | 0.001% | 250.88% |
| Tanshinone IIA | 0.025% | 188.31% |
| Tetrandine | 0.001% | 84.31% |
| Carvacrol | 0.0001% | 39.50% |
| cis-6-Noneol | 0.0010% | 60.84% |
| Retinyl punicate | 0.01% | 69.68% |
| Retinyl oleate | 0.01% | 60.21% |
| Equol | 0.001% | 220.36% |
|  | 0.0001% | 61.46% |
| MycoFusions Coriolus Black Corn Biomass | 0.10% | 27.55% |
| MycoFusions Maitake Waxy Hulless Barley Biomass | 0.10% | 24.28% |

TABLE 1-continued

| Paxillin Stimulator | Weight % | % increase in Paxillin (relative to control) |
|---|---|---|
| Zanthoxylum nitidium extract | 0.10% | 73.28% |
| Ophiopogon Thunb. PE extract | 0.01% | 115.21% |
| Radix platycodonis extract | 0.10% | 68.92% |
| Terminalia belerica extract | 0.01% | 260.09% |
| Cocculus glaucescens | 0.010% | 36.32% |
| Stephania solid extract | 0.10% | 104.08% |
| Rosemary PE 50% extract | 0.001% | 172.75% |

Fibroblasts treated with the indicated weight % of the various respective paxillin stimulators showed a significant % stimulation in mRNA levels, as indicated in Table 1.

Example 2: Stimulation of Paxillin Protein in Human Skin Biopsy

Compositions comprising a paxillin stimulator were each tested on 21 subject volunteers. For each paxillin stimulator, the composition was topically applied via a patch attached to the back of a randomly selected forearm of each of 21 volunteers, and a vehicle control was similarly applied to the back of the volunteer's forearm. After 3 weeks, the human skin biopsies were taken from the treated skin of the various volunteers and subjected to immunohistochemisty preparation. Paxillin protein level was demonstrated by specific antibody stain followed by microscopic examinations. Elevated protein level was determined for each treated subject by comparing to the vehicle control. Results were expressed as percentage of subjects that showed improvement.

Results for exemplary paxillin stimulators are presented in Table 2.

TABLE 2

| Paxillin Stimulator | Total No. of Subjects | No. Showing Improvement | % Subjects Improved |
|---|---|---|---|
| cis-6-Nonenol (%) | 21 | 15 | 71.4 |
| Lonchocarpus capassa extract (%) | 21[1] | 6 | 30.0 |

[1]Results were not able to be read for one subject treated with the topical composition comprising Lonchocarpus capassa extract.

As illustrated in Table 2, cis-6-nonenol showed increased paxillin levels in 71.4% of subjects tested; while Lonchocarpus capassa extract showed positive results in 30.0%.

Further, increase in paxillin protein was visibly observed in human skin biopsies. Representative photographs were taken from biopsy described above. FIGS. 1A and B demonstrate the results, where darker staining represent paxillin protein. As FIG. 1 illustrates, treatment with cis-6-Nonenol (B) increased paxillin protein in human skin as compared to treatment with a control (A).

Example 3: Exemplary Compositions

Cosmetic compositions comprising the paxillin stimulator cis-6-Nonenol for topical application to the skin are provided in Table 3 below.

TABLE 3

| Components | Composition: | | | |
| --- | --- | --- | --- | --- |
| | 1 | 2 | 3 | 4 |
| | Weight % | | | |
| paxillin stimulator (cis-6-Nonenol) | 0.0005 | 0.001 | 0.0015 | 0.002 |
| Acrylates/C10-30 Alkyl Acrylate Crosspolymer | 1 | 1 | 1 | 1 |
| Cetyl Ethylhexanoate | 10 | 10 | 10 | 10 |
| C12-15 Alkyl Benzoate | 3.9 | 3.9 | 3.9 | 3.9 |
| Isopropyl Isostearate | 3 | 3 | 3 | 3 |
| Diisopropyl dimer dillinoleate | 0.1 | 0.1 | 0.1 | 0.1 |
| Tocopheryl acetate | 0.5 | 0.5 | 0.5 | 0.5 |
| Butylene glycol | 2 | 2 | 2 | 2 |
| Propylene glycol | 1 | 1 | 1 | 1 |
| Dimethicone PEG-7 isostearate | 0.5 | 0.5 | 0.5 | 0.5 |
| Methyl gluceth-20 | 0.5 | 0.5 | 0.5 | 0.5 |
| Triethanolamine | 1 | 1 | 1 | 1 |
| Acrylates/acrylamide copolymer/mineral oil | 1.5 | 1.5 | 1.5 | 1.5 |
| DMDM Hydantoin/Iodopropynylbutylcarbonate | 0.4 | 0.4 | 0.4 | 0.4 |
| Deionized water | q.s. | q.s. | q.s. | q.s. |
| Total: | 100 | 100 | 100 | 100 |

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for treating wrinkles and/or fine lines comprising: topically applying to said wrinkle and/or fine line an effective amount of *Erythrina flabelliformis* extract or *Eclipta prostrata* extract in a cosmetically acceptable vehicle for a time sufficient to reduce severity of said wrinkle and/or fine lines.

2. A method for treating wrinkles and/or fine lines comprising: topically applying to said wrinkle and/or fine line an effective amount of *Echpta prostrata* extract in a cosmetically acceptable vehicle for a time sufficient to reduce severity of said wrinkle and/or fine lines.

3. The method according to claim 1, wherein said extract is soluble in water.

4. The method according to claim 2, wherein said extract is soluble in water.

5. The method according to claim 1, wherein said extract is soluble in ethanol.

6. The method according to claim 2, wherein said extract is soluble in ethanol.

7. The method according to claim 1, wherein said extract is soluble in a 50:50 ethanol:water mixture.

8. The method according to claim 2, wherein said extract is soluble in a 50:50 ethanol:water mixture.

* * * * *